(12) United States Patent
Kim et al.

(10) Patent No.: US 9,266,872 B2
(45) Date of Patent: Feb. 23, 2016

(54) 2-HYDROXYARYLAMIDE DERIVATIVE OR PHARMACEUTICALLY ACCEPTABLE SALT THEREOF, PREPARATION METHOD THEREOF, AND PHARMACEUTICAL COMPOSITION FOR PREVENTING OR TREATING CANCER CONTAINING SAME AS ACTIVE INGREDIENT

(71) Applicant: KOREA RESEARCH INSTITUTE OF BIOSCIENCE AND BIOTECHNOLOGY, Daejeon (KR)

(72) Inventors: Semi Kim, Daejeon (KR); Ill Young Lee, Daejeon (KR); Hye-Jin Min, Daejeon (KR); Eun-Hee Nam, Daejeon (KR); Pilho Kim, Daejeon (KR); Chang Soo Yun, Daejeon (KR); Dong Joon Ko, Daejeon (KR)

(73) Assignee: Korea Research Institute of Bioscience and Biotechnology (KR)

( * ) Notice: Subject to any disclaimer, the term of this patent is extended or adjusted under 35 U.S.C. 154(b) by 0 days.

(21) Appl. No.: 14/256,808

(22) Filed: Apr. 18, 2014

(65) Prior Publication Data
US 2014/0221411 A1    Aug. 7, 2014

Related U.S. Application Data

(63) Continuation-in-part of application No. PCT/KR2012/008626, filed on Oct. 19, 2012.

(30) Foreign Application Priority Data

Oct. 21, 2011  (KR) .................. 10-2011-0107934
Oct. 19, 2012  (KR) .................. 10-2012-0116733

(51) Int. Cl.
| | |
|---|---|
| A61K 31/167 | (2006.01) |
| A61K 31/426 | (2006.01) |
| C07D 417/04 | (2006.01) |
| C07D 215/38 | (2006.01) |
| C07D 285/135 | (2006.01) |
| C07D 213/75 | (2006.01) |
| C07D 239/42 | (2006.01) |
| C07D 277/46 | (2006.01) |
| C07D 213/82 | (2006.01) |
| C07D 215/56 | (2006.01) |
| C07D 277/82 | (2006.01) |
| A61K 31/4439 | (2006.01) |
| A61K 31/428 | (2006.01) |
| A61K 31/433 | (2006.01) |
| A61K 31/44 | (2006.01) |
| A61K 31/4709 | (2006.01) |
| A61K 31/505 | (2006.01) |
| A61K 31/5377 | (2006.01) |

(52) U.S. Cl.
CPC ............ *C07D 417/04* (2013.01); *A61K 31/167* (2013.01); *A61K 31/426* (2013.01); *A61K 31/428* (2013.01); *A61K 31/433* (2013.01); *A61K 31/44* (2013.01); *A61K 31/4439* (2013.01); *A61K 31/4709* (2013.01); *A61K 31/505* (2013.01); *A61K 31/5377* (2013.01); *C07D 213/75* (2013.01); *C07D 213/82* (2013.01); *C07D 215/38* (2013.01); *C07D 215/56* (2013.01); *C07D 239/42* (2013.01); *C07D 277/46* (2013.01); *C07D 277/82* (2013.01); *C07D 285/135* (2013.01)

(58) Field of Classification Search
CPC . A61K 31/167; A61K 31/426; A61K 31/433; A61K 31/44; A61K 31/4709
USPC .................. 514/313, 344, 363, 371, 617, 619
See application file for complete search history.

(56) References Cited

U.S. PATENT DOCUMENTS

| | | | |
|---|---|---|---|
| 2006/0014811 A1 * | 1/2006 | Muto et al. .................... | 514/369 |
| 2007/0042997 A1 * | 2/2007 | Itai et al. ....................... | 514/63 |

FOREIGN PATENT DOCUMENTS

| | | | |
|---|---|---|---|
| JP | 62-099329 A | | 5/1987 |
| WO | WO 01-98290 A2 | | 12/2001 |
| WO | WO 02-076918 A1 | | 10/2002 |
| WO | WO 03-103655 A1 | | 12/2003 |
| WO | WO 2013/058613 | * | 4/2013 |

OTHER PUBLICATIONS

Johnson et al., Relationships between drug activity in NCI preclinical in vitro and in vivo models and early clinical trials, British Journal of Cancer, 84(10):1424-1431, 2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1101 O, 1995.*
Gura et al., Systems for identifying new drugs are often faulty, Science, 278:1041-1042, 1997.*
Itai et al., CAPLUS Abstract 142:148826 (2005).*
Kang et al., Discovery of novel 2-hydroxydiarylamide derivatives as TMPRSS4 inhibitors, Bioorganic & Medicinal Chemistry Letters, vol. 23, Issue 6, pp. 1748-1751 (Mar. 2013).*
Aberasturi et al., TMPRSS4: an emerging potential therapeutic target in cancer, British Journal of Cancer, 112, pp. 4-8, (2015).*
Li et al., Suppressino of cancer relapse and metastasis by inhibiting cancer stemness, PNAS, vol. 112, No. 6, pp. 1839-1844 (2015).*
International Search Report prepared by the Korean Intellectual Property Office on Mar. 21, 2013, for International Application No. PCT/KR2012/008626.

* cited by examiner

*Primary Examiner* — Deepak Rao
(74) *Attorney, Agent, or Firm* — Sheridan Ross P.C.

(57) ABSTRACT

The present invention relates to a 2-hydroxyarylamide derivative or a pharmaceutically acceptable salt thereof, a preparation method thereof, and a pharmaceutical composition for preventing or treating cancer comprising the same as an active ingredient. The 2-hydroxyarylamide derivative prepared by the present invention is excellent in the inhibition of the activity of TMPRSS4 serine protease and the suppression of the infiltration of TMPRSS4-expressed cancer cells, and thus can be useful as a composition for preventing or treating cancer by inhibiting TMPRSS4 over-expressed in cancer cells, particularly, colorectal cancer, lung cancer, breast cancer, prostate cancer, ovarian cancer, pancreatic cancer, or stomach cancer cells.

2 Claims, 4 Drawing Sheets

ECS: enterokinase cleavage site
TMPRSS4PD: TMPRSS4 protease domain (205Val..437Leu)

1:size marker
2:protease activated by enterokinase

SEQUENCE LISTING

```
<160> NUMBER OF SEQ ID NOS: 2

<210> SEQ ID NO 1
<211> LENGTH: 68
<212> TYPE: DNA
<213> ORGANISM: Artificial
<220> FEATURE:
<223> OTHER INFORMATION: primer

<400> SEQUENCE: 1
tcatatggat tacaaagacg atgacggtga ctacaaagat gacgacgata aggtggtggg    60
tggggagg                                                              68

<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2
gaatctcgag cagctcagcc ttccagacat                                      30
```

2-HYDROXYARYLAMIDE DERIVATIVE OR PHARMACEUTICALLY ACCEPTABLE SALT THEREOF, PREPARATION METHOD THEREOF, AND PHARMACEUTICAL COMPOSITION FOR PREVENTING OR TREATING CANCER CONTAINING SAME AS ACTIVE INGREDIENT

CROSS REFERENCE TO RELATED APPLICATIONS

This application is a Continuation-in-Part of PCT Application No. PCT/KR2012/008626 having an international filing date of 19 Oct. 2012, which designated the United States, which PCT application claimed the benefit of Korean Patent Application No. 10-2011-0107934 filed Oct. 21, 2011, and Korean Patent Application No. 10-2012-0116733 filed 19 Oct. 2012, the disclosures of which are incorporated herein by reference.

REFERENCE TO SEQUENCE LISTING

This application contains a Sequence Listing submitted as an electronic text file named "14fpo_03_009_ST25.txt", having a size in bytes of 2 KB, and created on Apr. 18, 2014. The information contained in this electronic file is hereby incorporated by reference in its entirety pursuant to 37 CFR §1.52(e)(5).

BACKGROUND OF THE INVENTION

1. Field of the Invention

The present invention relates to the method for treatment of cancer using 2-hydroxyarylamide derivative or a pharmaceutically acceptable salt thereof.

2. Description of the Related Art

In the clinical treatment of cancer patients, side effects accompanied particularly by chemo-therapy and radio-therapy are the major problem. So, it is an urgent request to develop an anticancer agent to reduce side effects accompanied by chemo-therapy. If only the gene products only expressed or specifically over-expressed in cancer cells are identified and if their expressions are inhibited without destroying cell differentiation or cell metabolism in normal cells, an anticancer agent that kills cancer cells specifically without destroying normal cells would be developed based on that. Thus, it is regarded as a promising method for the development of an anticancer agent having excellent therapeutic effect with less side effects to identify a protein expressed by an oncogene or a tumor suppressor gene inducing abnormal functioning of signal transduction pathway so as to convert the malfunctioning signal transduction pathway into normal functioning one.

In particular, the importance of a protease as a tumor and cancer related factor is increased day by day. Cell growth, angiogenesis, infiltration, migration, metastasis, survival, expansion, and progression of cancer cells are all mediated by signal transduction control system and proteolytic activities of various proteases. One of the most peculiar phenomenon is degradation and remodeling of extracellular matrix composing intercellular space matrix and basement membrane by unregulated protease. Cancer cells infiltrate into the neighboring tissues locally and far away by the said system. Infiltration and metastasis of cancer cells are clinically very important factors to determine the treatment prognosis of cancer patients.

Infiltration of cancer cells composed of three serial steps of adhesion, degradation of basement membrane, and migration is essential not only for metastasis but also for angiogenesis. For example in metastasis, cancer cell infiltration is inevitable process for cancer cells to migrate into blood stream or to other tissues through blood stream. Precisely, cancer cells are adhered on the adhesion molecule expressed on basement membrane and then induce the secretion of various proteases to decompose the basement membrane thereon, leading to the migration through the broken basement membrane. Marimastat, the inhibitor belonging to matrix metalloproteinase family, which is involved in the protein decomposition essential for cell infiltration, has been known to inhibit metastasis and angiogenesis as well by inhibiting cancer cell infiltration.

Therefore, protease can regulate cancer cell metastasis and those genes involved in the same can be used as cancer prognostic markers, suggesting that protease or those genes involved in the same are important targets of cancer treatment. The most representative metastasis related proteins are MMPs (matrix metalloproteinases), cathepsin B, cathepsin D, and serine protease including uPA (urokinase plasminogen activator) (non-patent reference 1). Among many proteases, TMPRSS4 has recently been identified in its biological functions to cancer (non-patent reference 2). According to the recent reports, TMPRSS4 is an important mediator for infiltration, metastasis, migration, and adhesion as well as EMP (epithelial mesenchymal transition) in human epithelial cancer cells. It has been pointed therefore that TMPRSS4 has a great potential as a target of cancer treatment. Nevertheless, studies on TMPRSS4 are not plenty enough. Considering the great potential of TMPRSS4 as a powerful and independent prognostic marker and as a target for the development of an inhibitor of infiltration and metastasis, it is also important to develop TMPRSS4 inhibitor as an anticancer target.

TMPRSS4 gene is also over-expressed in malignant thyroid neoplasms. Therefore, The gene is proposed as a diagnostic and prognostic marker in such types of cancer (non-patent references 3 and 4).

Up to date, various compositions for treating cancer have been studied, which have been mainly focused on the inhibition of cancer specific marker. However, the studies on TMPRSS4 considered as a target of cancer treatment have not been actively undergoing.

The present inventors have studied to develop an anticancer agent to inhibit metastasis by suppressing cancer cell infiltration by inhibiting TMPRSS4 over-expressed specifically in cancer cells. In the course of the study, the inventors prepared a 2-hydroxyarylamide derivative and confirmed that the compound had excellent effect of inhibiting TMPRSS4, leading to the completion of this invention.

SUMMARY OF THE INVENTION

It is an object of the present invention to provide a 2-hydroxyayrlamide derivative or a pharmaceutically acceptable salt thereof.

It is another object of the present invention to provide a preparation method of the 2-hydroxyarylamide derivative.

It is also an object of the present invention to provide a pharmaceutical composition for preventing or treating cancer which comprises the 2-hydroxyarylamide derivative or the pharmaceutically acceptable salt thereof as an active ingredient.

It is further an object of the present invention to provide a pharmaceutical composition for inhibiting TMPRSS4 (transmembrane protease serine-4) which comprises the 2-hydroxyarylamide derivative or the pharmaceutically acceptable salt thereof as an active ingredient.

To achieve the above objects, the present invention provides a 2-hydroxyarylamide derivative represented by the below Formula 1 or a pharmaceutically acceptable salt thereof:

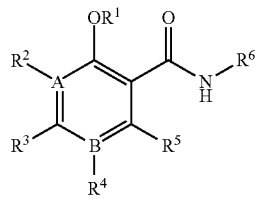

[Formula 1]

($R^1$~$R^6$, A and B are as defined in this description).

Further, the present invention provides a preparation method of the 2-hydroxyarylamide derivative represented by the above Formula 1.

The present invention also provides a pharmaceutical composition for preventing or treating cancer which comprises the 2-hydroxyarylamide derivative represented by the above Formula 1 or the pharmaceutically acceptable salt thereof as an active ingredient.

In addition, the present invention provides a pharmaceutical composition for inhibiting TMPRSS4 (transmembrane protease serine-4) which comprises the 2-hydroxyarylamide derivative represented by the above Formula 1 or the pharmaceutically acceptable salt thereof as an active ingredient.

Advantageous Effect

As explained hereinbefore, the 2-hydroxyarylamide derivative compound prepared in this invention has the effect of inhibiting the activity of TMPRSS4 serine protease and suppressing the infiltration of cancer cells expressing TMPRSS4, so that it can be useful as a composition for preventing or treating cancer by inhibiting TMPRSS4 overexpressed in cancer cells, particularly, colorectal cancer, lung cancer, breast cancer, prostate cancer, ovarian cancer, pancreatic cancer, or stomach cancer cells.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
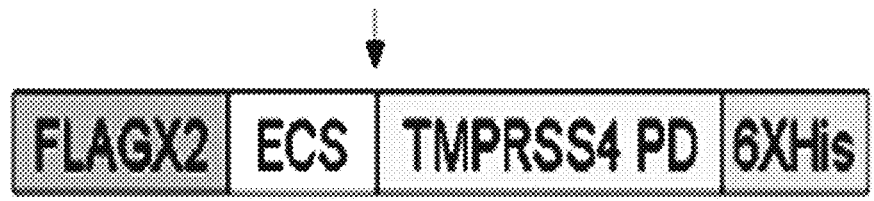
FIG. 1 is a diagram illustrating the cleavage site of FlagX2-enterokinase inserted in N-terminal of TMPRSS4 serine protease domain of Experimental Example 1.

Hereinafter, the present invention is described in detail.

The present invention provides a 2-hydroxyarylamide derivative represented by the below Formula 1 or a pharmaceutically acceptable salt thereof.

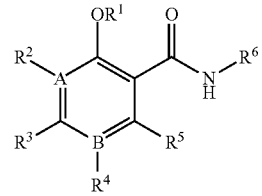

[Formula 1]

In Formula 1, $R^1$ is hydrogen, $C_1$-$C_6$ straight or branched alkylcarbonyl or benzyl, $R^2$, $R^3$, $R^4$, and $R^5$ are independently hydrogen, halogen, $C_1$-$C_6$ straight or branched alkyl, $C_1$-$C_6$ straight or branched alkoxy, $C_1$-$C_6$ straight or branched haloalkyl, nitro, cyano, hydroxy, amino, aminocarbonyl, $C_1$-$C_6$ straight or branched alkylcarbonylamino, and $C_5$-$C_7$ aryl substituted with one or more halogens, $R^2$ and $R^3$ can form $C_5$-$C_7$ aryl or heteroaryl along with atoms which are conjugated to the same, $R^6$ is unsubstituted $C_5$-$C_7$ aryl or $C_5$-$C_7$ aryl substituted with one or more compounds selected from the group consisting of halogen, $C_1$-$C_6$ straight or branched alkyl, $C_1$-$C_6$ straight or branched alkoxy, $C_1$-$C_6$ straight or branched haloalkyl, cyano, amino, and nitro; or $C_5$-$C_{12}$ monocyclic or bicyclic heteroaryl substituted with one or more compounds selected from the group consisting of halogen, $C_1$-$C_6$ straight or branched alkyl, $C_1$-$C_6$ straight or branched haloalkyl, and $C_5$-$C_7$ aryl. At this time, the said heteroaryl can include one or more hetero atoms selected from the group consisting of N, P, and S, and A and B are independently carbon (C) or nitrogen (N), and at this time both A and B can not be nitrogen at the same time.

Preferably, $R^1$ is hydrogen, $C_1$-$C_4$ straight or branched alkylcarbonyl or benzyl, $R^2$, $R^3$, $R^4$, and $R^5$ are independently hydrogen, halogen, $C_1$-$C_4$ straight or branched alkyl, $C_1$-$C_4$ straight or branched alkoxy, $C_1$-$C_4$ straight or branched haloalkyl, nitro, cyano, hydroxy, amino, aminocarbonyl, $C_1$-$C_4$ straight or branched alkylcarbonylamino, and phenyl substituted with one or more halogens, $R^2$ and $R^3$ can form $C_5$-$C_7$ aryl along with atoms which are conjugated to the same, $R^6$ is unsubstituted phenyl or phenyl substituted with one or more compounds selected from the group consisting of halogen, $C_1$-$C_4$ straight or branched alkyl, $C_1$-$C_4$ straight or branched alkoxy, $C_1$-$C_4$ straight or branched haloalkyl, cyano, amino, and nitro; or pyridine, pyrimidine, thiazole, thiadiazole or isoquinoline substituted with one or more compounds selected from the group consisting of halogen, $C_1$-$C_4$ straight or branched alkyl, $C_1$-$C_4$ straight or branched haloalkyl, and $C_5$-$C_7$ aryl, and A and B are independently carbon (C) or nitrogen (N), and at this time both A and B can not be nitrogen at the same time.

More preferably, $R^1$ is hydrogen, acetyl or benzyl, $R^2$ is hydrogen, halogen, methyl or ethyl, $R^3$ is hydrogen, halogen or trifluoromethyl, $R^2$ and $R^3$ can form phenyl along with atoms which are conjugated to the same, $R^4$ is a compound selected from the group consisting of hydrogen, halogen, methyl, ethyl, methoxy, ethoxy, nitro, cyano, amino, methylcarbonylamino, aminocarbonyl and 2,4-difluorophenyl, $R^5$ is hydrogen,
$R^6$ is a compound selected from the group consisting of
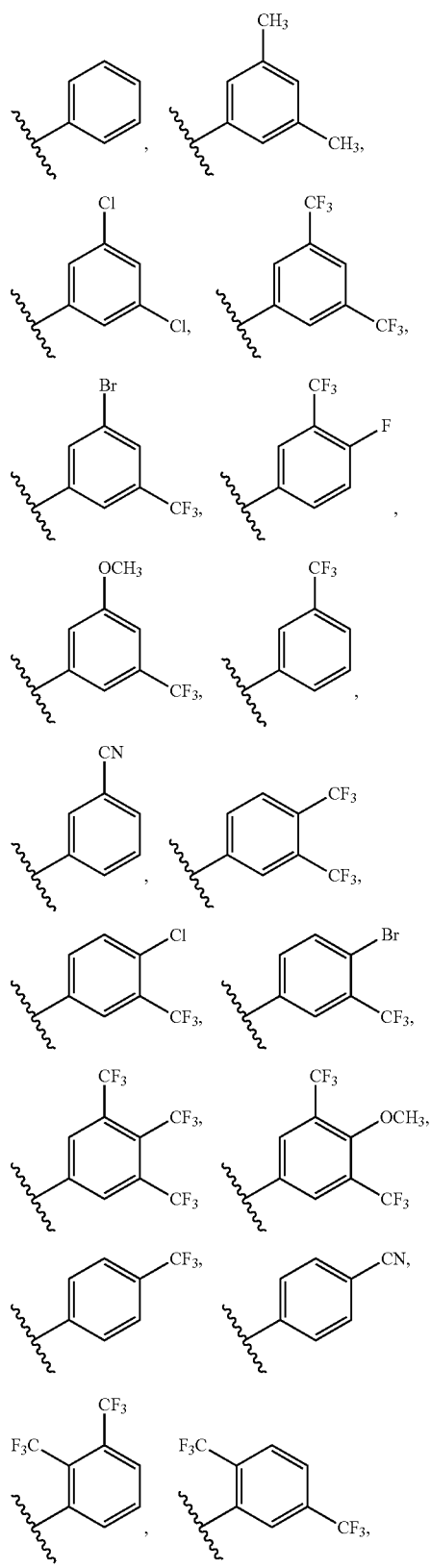
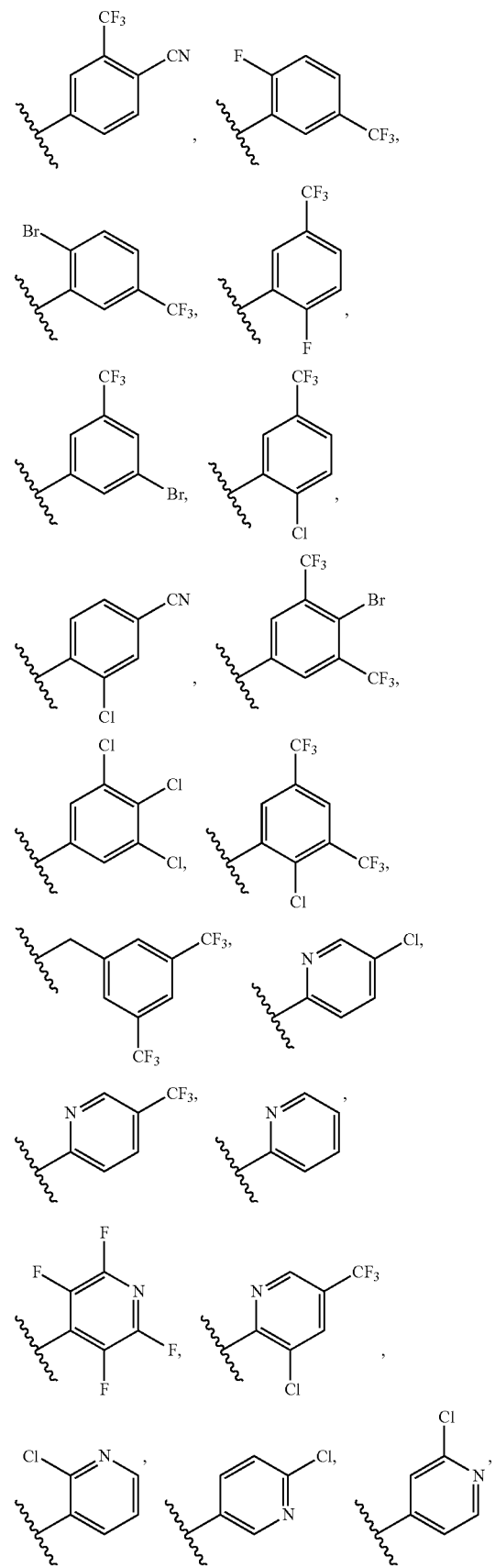

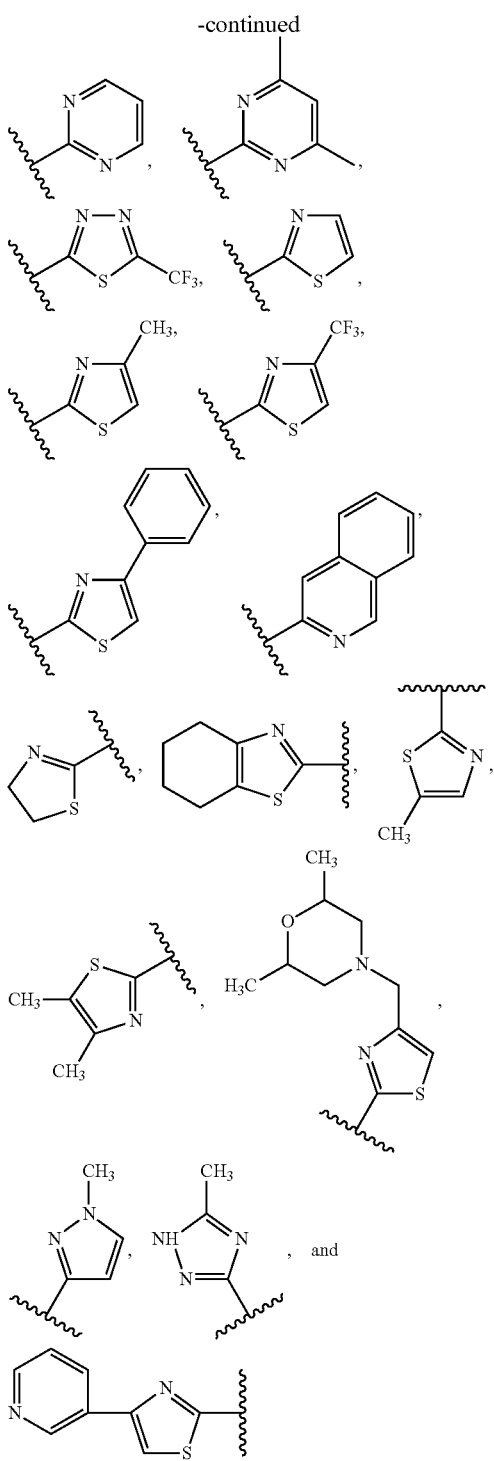

and

A and B are independently carbon (C) or nitrogen (N), and at this time both A and B can not be nitrogen at the same time.

The 2-hydroxyarylamide derivative represented by Formula 1 is more specifically exemplified by followings:

(1) N-(3,5-bis(trifluoromethyl)phenyl)-5-chloro-2-hydroxybenzamide;
(2) N-(3,5-bis(trifluoromethyl)phenyl)3,5-dichloro-2-hydroxybenzamide;
(3) N-(3,5-bis(trifluoromethyl)phenyl)-2-hydroxy-5-methylbenzamide;
(4) 5-chloro-N-(4-fluoro-3-(trifluoromethyl)phenyl)-2-hydroxybenzamide;
(5) N-(3,5-bis(trifluoromethyl)phenyl)-2-hydroxybenzamide;
(6) 5-chloro-2-hydroxy-N-(3-methoxy-5-(trifluoromethyl)phenyl)benzamide;
(7) N-(3,5-bis(trifluoromethyl)phenyl)-2-hydroxy-5-methoxybenzamide;
(8) N-(3,5-bis(trifluoromethyl)phenyl)-3-hydroxy-2-naphthaamide;
(9) N-(3,5-bis(trifluoromethyl)phenyl)-5-bromo-2-hydroxybenzamide;
(10) 5-chloro-N-(3-(trifluoromethyl)phenyl)-2-hydroxybenzamide;
(11) 5-chloro-N-(3-cyanophenyl)-2-hydroxybenzamide;
(12) 5-chloro-N-(4-cyanophenyl)-2-hydroxybenzamide;
(13) N-(3,5-bis(trifluoromethyl)phenyl)-4-(trifluoromethyl)-2-hydroxybenzamide;
(14) N-(3,5-bis(trifluoromethyl)phenyl)-5-fluoro-2-hydroxybenzamide;
(15) 5-chloro-N-(4-(trifluoromethyl)phenyl)-2-hydroxybenzamide;
(16) N-(4-bromo-3-(trifluoromethyl)phenyl)-5-chloro-2-hydroxybenzamine;
(17) 5-chloro-N-(3-(trifluoromethyl)-2-methylphenyl)-2-hydroxybenzamide;
(18) N-(2,5-bis(trifluoromethyl)phenyl)-5-chloro-2-hydroxybenzamine;
(19) 5-chloro-N-(4-cyano-3-(trifluoromethyl)phenyl)-2-hydroxybenzamide;
(20) N-(2-bromo-5-(trifluoromethyl)phenyl)-5-chloro-2-hydroxybenzamide;
(21) 5-chloro-N-(2-fluoro-5-(trifluoromethyl)phenyl)-2-hydroxybenzamide;
(22) N-(3-bromo-5-(trifluoromethyl)phenyl)-5-chloro-2-hydroxybenzamide;
(23) 5-chloro-N-(2-chloro-5-(trifluoromethyl)phenyl)-2-hydroxybenzamide;
(24) N-(3,5-bis-trifluoromethyl-benzyl)-5-chloro-2-hydroxy-benzamide;
(25) 5-chloro-2-hydroxy-N-quinoline-3-yl-benzamide;
(26) N-(3,5-bis-trifluoromethyl-phenyl)-3-chloro-2-hydroxy-benzamide;
(27) 5-chloro-N-(2-chloro-4-cyano-phenyl)-2-hydroxybenzamide;
(28) 5-chloro-2-hydroxy-N-(5-trifluoromethyl-[1,3,4]thiadiazole-2-yl)-benzamide;
(29) 5-chloro-N-(2-chloro-3,5-bis-trifluoromethyl-phenyl)-2-hydroxy-benzamide;
(30) N-(2-chloro-3,5-bis(trifluoromethyl)phenyl)-4',6'-difluoro-4-hydroxybiphenyl-3-carboxyamide;
(31) 5-amino-N-(3,5-bis(trifluoromethyl)phenyl)-2-hydroxybenzamide;
(32) 5-chloro-N-(4-chloro-3-(trifluoromethyl)phenyl)-2-hydroxybenzamide;
(33) 5-chloro-2-hydroxy-N-(4-methyl-3,5-bis(trifluoromethyl)phenyl)benzamide;
(34) N-(3,5-bis(trifluoromethyl)phenyl)-5-chloro-2-hydroxy-3-methylbenzamide;
(35) 5-acetoamido-N-(3,5-bis(trifluoromethyl)phenyl)-2-hydroxybenzamide;
(36) 5-chloro-2-hydroxy-N-(2-nitro-4-trifluoromethyl-phenyl)-benzamide;
(37) 5-chloro-N-(5-cyano-pyridine-2-yl)-2-hydroxy-benzamide;
(38) N3-(3,5-bis-trifluoromethyl-phenyl)-4-hydroxy-isophthalamide;

(39) 5-chloro-2-hydroxy-N-(4-methoxy-3,5-bis-trifluoromethyl-phenyl)-benzamide;
(40) 5-chloro-2-hydroxy-N-(pyridine-2-yl)benzamide;
(41) 5-chloro-2-hydroxy-N-(5-(trifluoromethyl)pyridine-2-yl)benzamide;
(42) 5-chloro-N-(5-chloropyridine-2-yl)-2-hydroxybenzamide;
(43) 5-chloro-2-hydroxy-N-(perfluoropyridine-4-yl)benzamide;
(44) 5-chloro-N-(2-chloropyridine-3-yl)-2-hydroxybenzamide;
(45) 5-chloro-N-(6-chloropyridine-3-yl)-2-hydroxybenzamide;
(46) 5-chloro-N-(3-chloro-5-(trifluoromethyl)pyridine-2-yl)-2-hydroxybenzamide;
(47) 5-chloro-N-(2-chloropyridine-4-yl)-2-hydroxybenzamide;
(48) 5-chloro-N-(4,6-dimethylpyrimidine-2-yl)-2-hydroxybenzamide;
(49) 5-chloro-2-hydroxy-N-(pyrimidine-2-yl)benzamide;
(50) 5-chloro-2-hydroxy-N-(4-methylthiazole-2-yl)benzamide;
(51) 5-chloro-2-hydroxy-N-(thiazole-2-yl)benzamide;
(52) 5-chloro-2-hydroxy-N-(4-(trifluoromethyl)thiazole-2-yl)benzamide;
(53) 5-chloro-2-hydroxy-N-(4-phenylthiazole-2-yl)benzamide;
(54) N-(3,5-bis(trifluoromethyl)phenyl)-4-chloro-2-hydroxybenzamide;
(55) N-(3,5-bis(trifluoromethyl)phenyl)-2-hydroxy-5-nitrobenzamide;
(56) N-(3,5-bis(trifluoromethyl)phenyl)-5-cyano-2-hydroxybenzamide;
(57) 2-(3,5-bis(trifluoromethyl)phenylcarbamoyl)-4-chlorophenylacetate;
(58) 2-benzyloxy-N-(3,5-bis-trifluoromethyl-phenyl)-5-chlorobenzamide;
(59) 5-chloro-2-hydroxy-N-phenylbenzamide;
(60) 5-chloro-N-(3,5-dimethylphenyl)-2-hydroxybenzamide;
(61) 5-chloro-N-(3,5-dichlorophenyl)-2-hydroxybenzamide;
(62) N-(3,4-bis(trifluoromethyl)phenyl)-5-chloro-2-hydroxybenzamide;
(63) N-(4-bromo-3-(trifluoromethyl)phenyl)-5-chloro-2-hydroxybenzamide;
(64) 5-chloro-N-(2-fluoro-5-(trifluoromethyl)phenyl)-2-hydroxybenzamide;
(65) N-(4-bromo-3,5-bis(trifluoromethyl)phenyl)-5-chloro-2-hydroxybenzamide;
(66) 5-chloro-2-hydroxy-N-(3,4,5-trichloro-phenyl)benzamide;
(67) N-(3,5-bis(trifluoromethyl)phenyl)-5-chloro-2-hydroxynicotineamide;
(68) N-(3,5-bis(trifluoromethyl)phenyl)-4-hydroxyquinoline-3-carboxyamide;
(69) 5-chloro-N-(4,5-dihydrothiazol-2-yl)-2-hydroxybenzamide;
(70) 5-chloro-2-hydroxy-N-(4,5,6,7-tetrahydrobenzo[d]thiazol-2-yl)benzamide;
(71) 5-chloro-2-hydroxy-N-(5-methylthiazole-2-yl)benzamide;
(72) 5-chloro-N-(4,5-dimethylthiazol-2-yl)-2-hydroxybenzamide;
(73) 5-chloro-N-(4-((2,6-dimethylmorpholino)methyl)thiazol-2-yl)-2-hydroxybenzamide;
(74) 5-chloro-2-hydroxy-N-(1-methyl-1H-pyrazol-3-yl)benzamide;
(75) 5-chloro-2-hydroxy-N-(5-methyl-1H-1,2,4-triazol-3-yl)benzamide; and
(76) 5-chloro-2-hydroxy-N-(4-(pyridin-3-yl)thiazol-2-yl)benzamide.

The preferable structure of the 2-hydroxyarylamide derivative represented by Formula of the present invention is presented in Table 1.

TABLE 1

| No. | Structural Formula |
|---|---|
| 1 | 5-chloro-2-hydroxy-N-(3,5-bis(trifluoromethyl)phenyl)benzamide |
| 2 | N-(3,5-bis(trifluoromethyl)phenyl)-3,5-dichloro-2-hydroxybenzamide |
| 3 | N-(3,5-bis(trifluoromethyl)phenyl)-2-hydroxy-5-methylbenzamide |
| 4 | 5-chloro-N-(4-fluoro-3-(trifluoromethyl)phenyl)-2-hydroxybenzamide |
| 5 | N-(3,5-bis(trifluoromethyl)phenyl)-2-hydroxybenzamide |

TABLE 1-continued

| No. | Structural Formula |
|---|---|
| 6 | 2-hydroxy-5-chloro-N-(3-methoxy-5-trifluoromethylphenyl)benzamide |
| 7 | 2-hydroxy-5-methoxy-N-(3,5-bis(trifluoromethyl)phenyl)benzamide |
| 8 | 3-hydroxy-N-(3,5-bis(trifluoromethyl)phenyl)-2-naphthamide |
| 9 | 2-hydroxy-5-bromo-N-(3,5-bis(trifluoromethyl)phenyl)benzamide |
| 10 | 2-hydroxy-5-chloro-N-(3-trifluoromethylphenyl)benzamide |
| 11 | 2-hydroxy-5-chloro-N-(3-cyanophenyl)benzamide |
| 12 | 2-hydroxy-5-chloro-N-(4-cyanophenyl)benzamide |
| 13 | 2-hydroxy-4-trifluoromethyl-N-(3,5-bis(trifluoromethyl)phenyl)benzamide |
| 14 | 2-hydroxy-5-fluoro-N-(3,5-bis(trifluoromethyl)phenyl)benzamide |
| 15 | 2-hydroxy-5-chloro-N-(4-trifluoromethylphenyl)benzamide |
| 16 | 2-hydroxy-5-chloro-N-(4-bromo-3-trifluoromethylphenyl)benzamide |
| 17 | 2-hydroxy-5-chloro-N-(2,3-bis(trifluoromethyl)phenyl)benzamide |

TABLE 1-continued
| No. | Structural Formula |
|---|---|
| 18 | 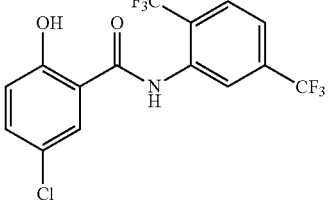 |
| 19 | 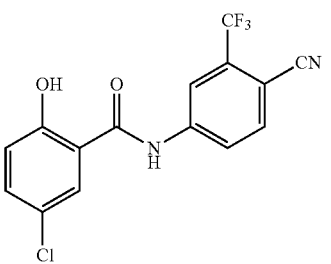 [SMILES: N#Cc1ccc(NC(=O)c2cc(Cl)ccc2O)cc1C(F)(F)F] |
| 20 | 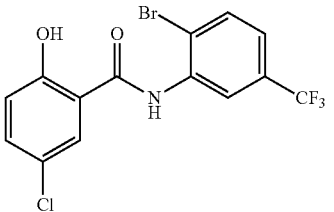 [SMILES: O=C(Nc1cc(C(F)(F)F)ccc1Br)c1cc(Cl)ccc1O] |
| 21 | 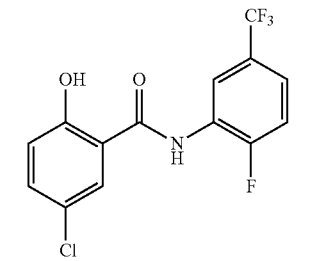 |
| 22 | 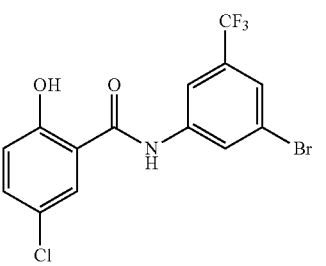 [SMILES: O=C(Nc1cc(Br)cc(C(F)(F)F)c1)c1cc(Cl)ccc1O] |
| 23 | 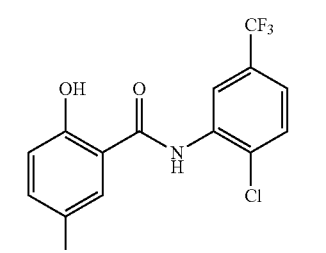 |
| 24 | 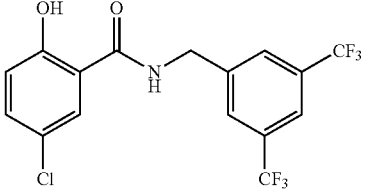 [SMILES: O=C(NCc1cc(C(F)(F)F)cc(C(F)(F)F)c1)c1cc(Cl)ccc1O] |
| 25 | 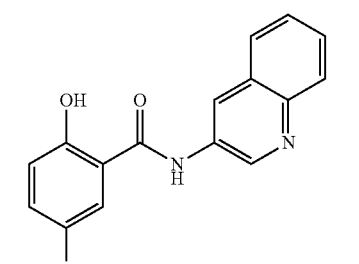 |
| 26 | 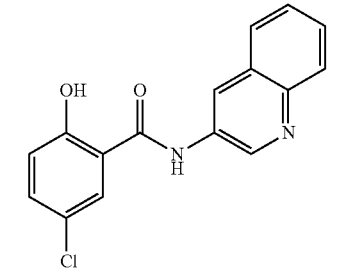 [SMILES: O=C(Nc1cnc2ccccc2c1)c1cc(Cl)ccc1O] |
| 27 | 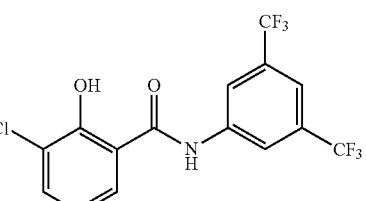 |
| 28 | 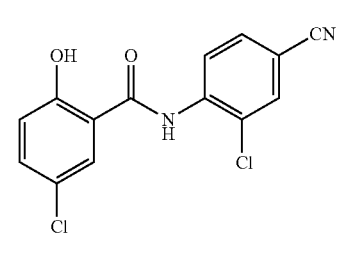 [SMILES: N#Cc1ccc(NC(=O)c2cc(Cl)ccc2O)c(Cl)c1] |
| 29 | 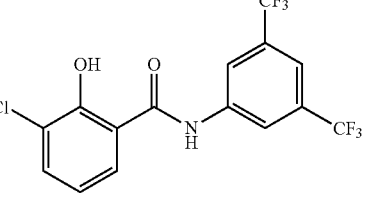 |

TABLE 1-continued

| No. | Structural Formula |
|---|---|
| 30 | 2-hydroxy-N-(3,5-bis(trifluoromethyl)phenyl... 2',4'-difluorobiphenyl-3-carboxamide |
| 31 | 5-amino-2-hydroxy-N-(3,5-bis(trifluoromethyl)phenyl)benzamide |
| 32 | 5-chloro-N-(4-chloro-3-(trifluoromethyl)phenyl)-2-hydroxybenzamide |
| 33 | 5-chloro-2-hydroxy-N-(3,5-bis(trifluoromethyl)-4-methylphenyl)benzamide |
| 34 | 5-chloro-2-hydroxy-3-methyl-N-(3,5-bis(trifluoromethyl)phenyl)benzamide |
| 35 | 5-acetamido-2-hydroxy-N-(3,5-bis(trifluoromethyl)phenyl)benzamide |
| 36 | 5-chloro-2-hydroxy-N-(2-nitro-4-(trifluoromethyl)phenyl)benzamide |
| 37 | 5-chloro-N-(5-cyanopyridin-2-yl)-2-hydroxybenzamide |
| 38 | 4-hydroxy-N1-(3,5-bis(trifluoromethyl)phenyl)benzene-1,3-dicarboxamide |
| 39 | 5-chloro-2-hydroxy-N-(3,5-bis(trifluoromethyl)-4-methoxyphenyl)benzamide |
| 40 | 5-chloro-2-hydroxy-N-(pyridin-2-yl)benzamide |

TABLE 1-continued
| No. | Structural Formula |
|---|---|
| 41 | 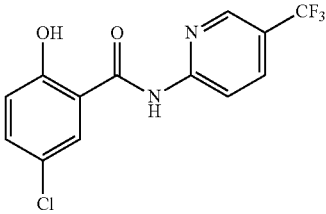 |
| 42 | 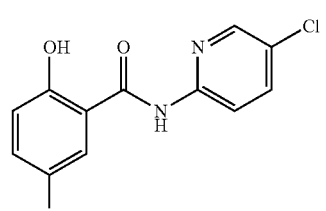 |
| 43 | 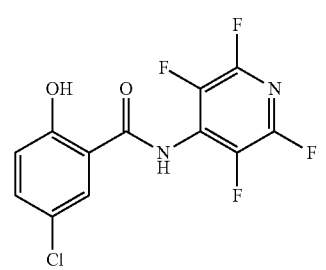 [SMILES: O=C(Nc1c(F)c(F)nc(F)c1F)c1cc(Cl)ccc1O] |
| 44 | 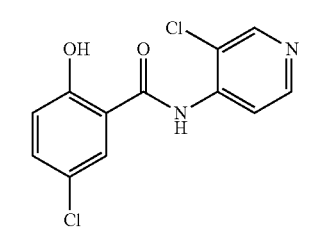 [SMILES: O=C(Nc1ccncc1Cl)c1cc(Cl)ccc1O] |
| 45 | 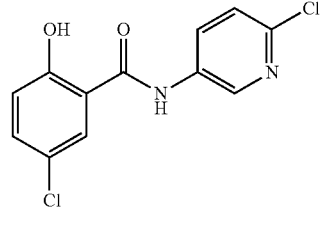 [SMILES: O=C(Nc1ccc(Cl)nc1)c1cc(Cl)ccc1O] |
| 46 | 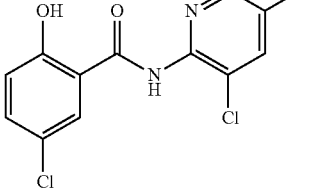 |
TABLE 1-continued
| No. | Structural Formula |
|---|---|
| 47 | 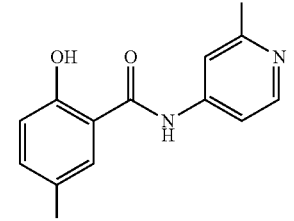 |
| 48 | 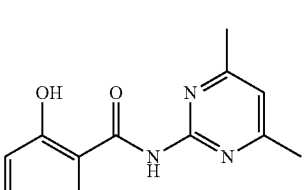 |
| 49 | 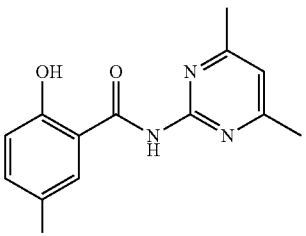 |
| 50 | 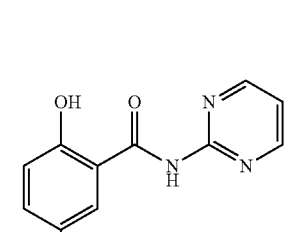 |
| 51 | 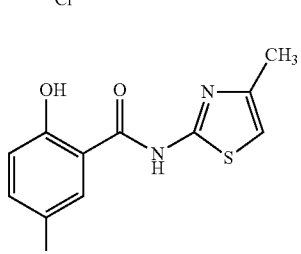 |
| 52 | 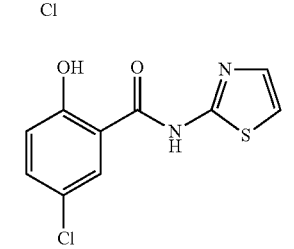 |

TABLE 1-continued

| No. | Structural Formula |
|-----|--------------------|
| 53  | 5-chloro-2-hydroxy-N-(4-phenylthiazol-2-yl)benzamide |
| 54  | 4-chloro-2-hydroxy-N-(3,5-bis(trifluoromethyl)phenyl)benzamide |
| 55  | 2-hydroxy-5-nitro-N-(3,5-bis(trifluoromethyl)phenyl)benzamide |
| 56  | 5-cyano-2-hydroxy-N-(3,5-bis(trifluoromethyl)phenyl)benzamide |
| 57  | 4-chloro-2-acetoxy-N-(3,5-bis(trifluoromethyl)phenyl)benzamide |
| 58  | 2-benzyloxy-5-chloro-N-(3,5-bis(trifluoromethyl)phenyl)benzamide |
| 59  | 5-chloro-2-hydroxy-N-phenylbenzamide |
| 60  | 5-chloro-2-hydroxy-N-(3,5-dimethylphenyl)benzamide |
| 61  | 5-chloro-2-hydroxy-N-(3,5-dichlorophenyl)benzamide |
| 62  | 5-chloro-2-hydroxy-N-(3,4-bis(trifluoromethyl)phenyl)benzamide |
| 63  | 5-chloro-2-hydroxy-N-(4-bromo-3-(trifluoromethyl)phenyl)benzamide |
| 64  | 5-chloro-2-hydroxy-N-(2-fluoro-5-(trifluoromethyl)phenyl)benzamide |

TABLE 1-continued
| No. | Structural Formula |
|---|---|
| 65 | 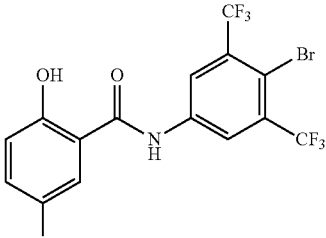 |
| 66 | 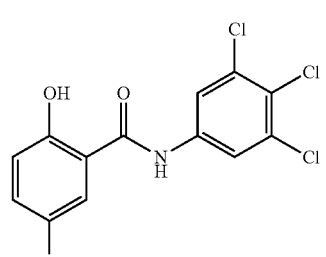 |
| 67 | 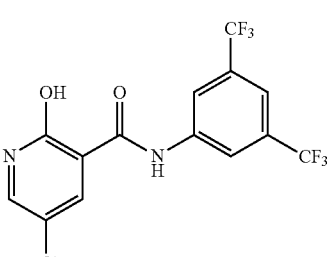 |
| 68 | 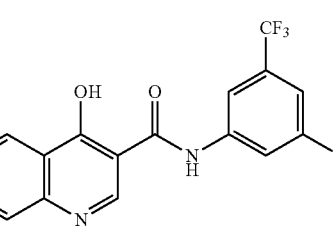 |
| 69 | 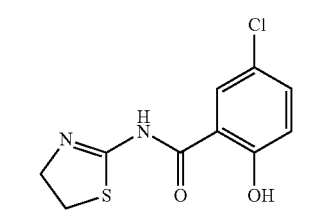 [SMILES: O=C(NC1=NCCS1)c1cc(Cl)ccc1O] |
| 70 | 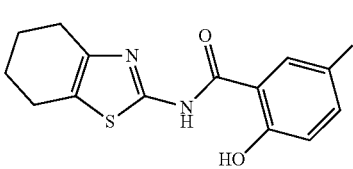 |
| 71 | 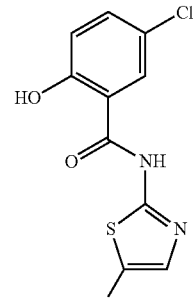 |
| 72 |  |
| 73 | 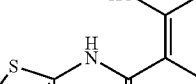 |
| 74 | 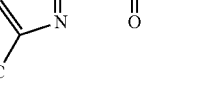 |

TABLE 1-continued

| No. | Structural Formula |
|-----|--------------------|
| 75 | (5-methyl-1H-1,2,4-triazol-3-yl)amide of 5-chloro-2-hydroxybenzoic acid) |
| 76 | (4-(pyridin-3-yl)thiazol-2-yl)amide of 5-chloro-2-hydroxybenzoic acid) |

The derivative of Formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, or phosphorous acid; or non-toxic organic acids such as aliphatic mono/di-carboxylate, phenyl-substituted alkanoate, hydroxy alkanoate/alkanedioate, aromatic acids, aliphatic and aromatic sulfonic acids. The pharmaceutically non-toxic salt is exemplified by sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutylate, caprate, heptanoate, propiolate, oxalate, malonate, succinate, suberate, sebacate, fumarate, maliate, butin-1,4-dioate, hexane-1,6-dioate, benzoate, chlorobenzoate, methylbenzoate, dinitro benzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, β-hydroxybutylate, glycolate, malate, tartrate, methanesulfonate, propanesulfonate, naphthalene-1-sulfonate, naphthalene-2-sulfonate, or mandelate.

The acid addition salt in this invention can be prepared by the conventional method known to those in the art. For example, the derivative of Formula 1 of the present invention is dissolved in an organic solvent such as methanol, ethanol, acetone, methylenechloride, and acetonitrile, followed by adding organic acid or inorganic acid. The obtained precipitate is filtered, and then dried to give acid addition salt. Or the precipitate is vacuum-distillated with a solvent and excessive acid, followed by drying or crystallization in an organic solvent to give acid addition salt.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention not only includes the 2-hydroxyarylamide derivative represented by Formula 1 but also includes the pharmaceutically acceptable salts thereof, every possible solvates, and hydrates constructed from the same.

In addition, the present invention provides a preparation method of the 2-hydroxyarylamide derivative represented by Formula 1.

Preparation Method 1

The preparation method of the derivative represented by Formula 1 of the present invention includes the step of preparing the compound of Formula 1 through amidation with the 2-hydroxyaryl acid compound represented by Formula 2 and the amine compound represented by Formula 3:

[Reaction Formula 1]

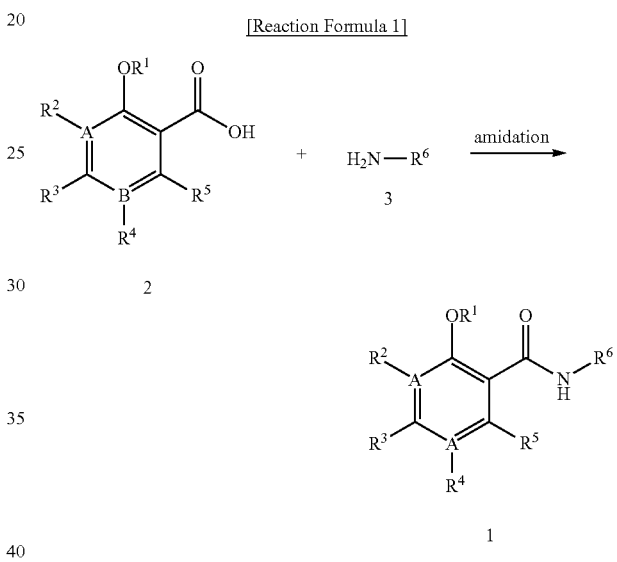

(In Reaction Formula 1, $R^1 \sim R^6$, A and B are as defined in Formula 1).

In the preparation method 1 of the present invention, the 2-hydroxyarylamide derivative represented by Formula 1 is prepared as follows: the 2-hydroxyaryl acid compound represented by Formula 2 and an amide synthesis reagent are dissolved in an organic solvent; the amine compound represented by Formula 3 is added thereto; and the mixture is stirred to give the 2-hydroxyarylamide derivative represented by Formula 1.

The said amide reagent can be diisopropylethylamine, triethylamine, dimethylaminopyridine (DMAP), benzotriazole-1-yl-oxy-tris(dimethylamino)-phosphoniumhexafluoro-phosphate (Py-BOP), O-benzotriazole-N,N,N,N-tetramethyl-uronium-hexafluoro-phosphate (HBTU), 2-(7-aza-1H-benzotriazole-1-yl)-1,1,3,3-tetramethyluroniumhexafluorophosphate (HATU), hydroxybenzotriazole (HOBt), dicyclohexylcarbodiimide (DCC), 1-ethyl-3-(3-dimethylaminopropyl)carbodiimide (EDC), or carbonyldiimidazole (CDI), and preferably hydroxybenzotriazole (HOBt) and/or O-benzotriazole-N,N,N,N-tetramethyl-uronium-hexafluoro-phosphate (HBTU).

The usable organic solvent herein is selected from the group consisting of methanol, dimethylformamide, tetrahydrofurane, dichloromethane, and toluene, which have no effect on the reaction, and preferably is dichloromethane.

Preparation Method 2

The preparation method of the derivative represented by Formula 1 of the present invention includes the step of preparing the compound of Formula 1 through coupling reaction with the 2-hydroxyaryl acid compound represented by Formula 2 and the amine compound represented by Formula 3 using a chlorinating agent:

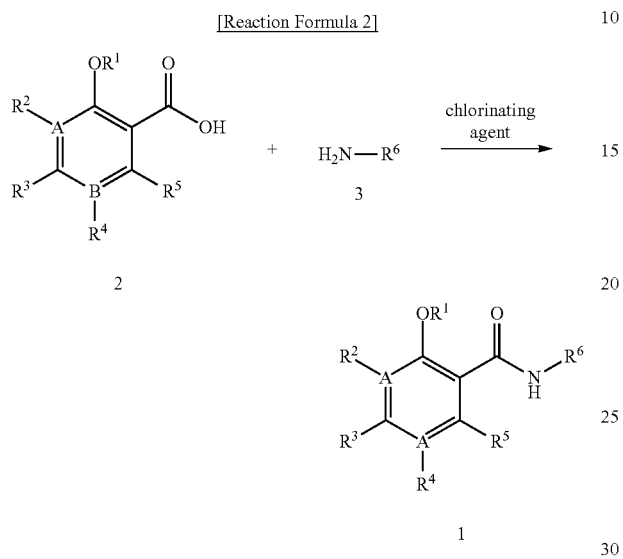

(In Reaction Formula 2, $R^1 \sim R^6$, A and B are as defined in Formula 1).

In the preparation method 2 of the present invention, the 2-hydroxyarylamide derivative represented by Formula 1 is prepared as follows: the 2-hydroxyaryl acid compound represented by Formula 2 is dissolved in an organic solvent in the presence of argon gas; a chlorinating agent is added thereto in the presence of a base; the amine compound represented by Formula 3 is added thereto; and the mixture is reflux-stirred to give the 2-hydroxyarylamide derivative represented by Formula 1.

The said chlorinating agent is selected from the group consisting of $PCl_3$, $POCl_3$, $SOCl_2$, $SO_2Cl_2$, and $COCl_2$, and is preferably $PCl_3$.

The base herein is selected from the group consisting of methylamine, ethylamine, dimethylamine, diethylamine, trimethylamine, triethylamine, cyclohexylamine, diethylisopropylamine, and pyridine, and is preferably pyridine or triethylamine, but not always limited thereto.

The usable organic solvent herein can be dichloromethane, chloroform, tetrahydrofurane, diethylether, toluene, xylene, benzene, chlorobenzene, or dimethylformamide, which has no effect on the reaction, and is preferably toluene.

The reaction temperature is not limited to a specific range, but the range from room temperature to boiling point of a solvent is preferred.

Preparation Method 3

The preparation method of the derivative represented by Formula 1 of the present invention, as shown in the below Reaction Formula 3, is composed of the following steps:

inducing coupling of the compound represented by Formula 2 and the amine compound represented by Formula 3 (step 1); and inducing deprotection of the protected hydroxy group of the compound represented by Formula 6 prepared in step (step 2).

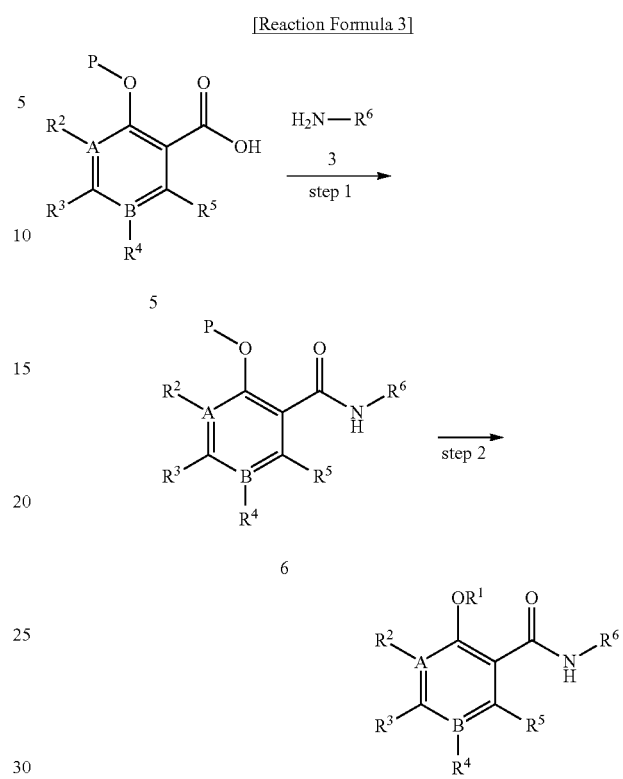

(In Reaction Formula 3, $R^1$ is hydrogen, $R^2 \sim R^6$, A and B are as defined in Formula 1, and P is a protecting group).

In step 1 of the preparation method 3 of the present invention, the compound represented by Formula 6 is prepared as follows: the aryl acid compound having protected hydroxy group represented by Formula 5 is dissolved in an organic solvent in the presence of argon gas; the amine compound represented by Formula 3 is added thereto; and the mixture is reflux-stirred to give the compound represented by Formula 6.

At this time, the conditions for the coupling reaction of step 1 are as described in the preparation method 2.

The protecting group P to protect hydroxy group is methyl group, t-butyl group, benzyl group, acetyl group, phenylcarbonyl group, pivaloyl group, t-butyldimethylsilyl (TBDMS) group, t-butyldiphenylsilyl (TBDPS) group, or methoxymethyl (MOM) group.

In step 2, the hydroxy group of the compound represented by Formula 6 prepared in step 1 is deprotected to give the compound represented by Formula 1b.

The deprotection is performed by the conventional method generally used in this field to deprotect the hydroxy group protected by the protecting group P.

Preparation Method 4

The preparation method of the derivative represented by Formula 1 of the present invention, as shown in the below Reaction Formula 4, is composed of the following steps:

inducing coupling of the 2-hydroxyaryl acid compound represented by Formula 2a and the amine compound represented by Formula 3 (step 1); and inducing reduction of the compound represented by Formula 1a prepared in step 1 (step 2).

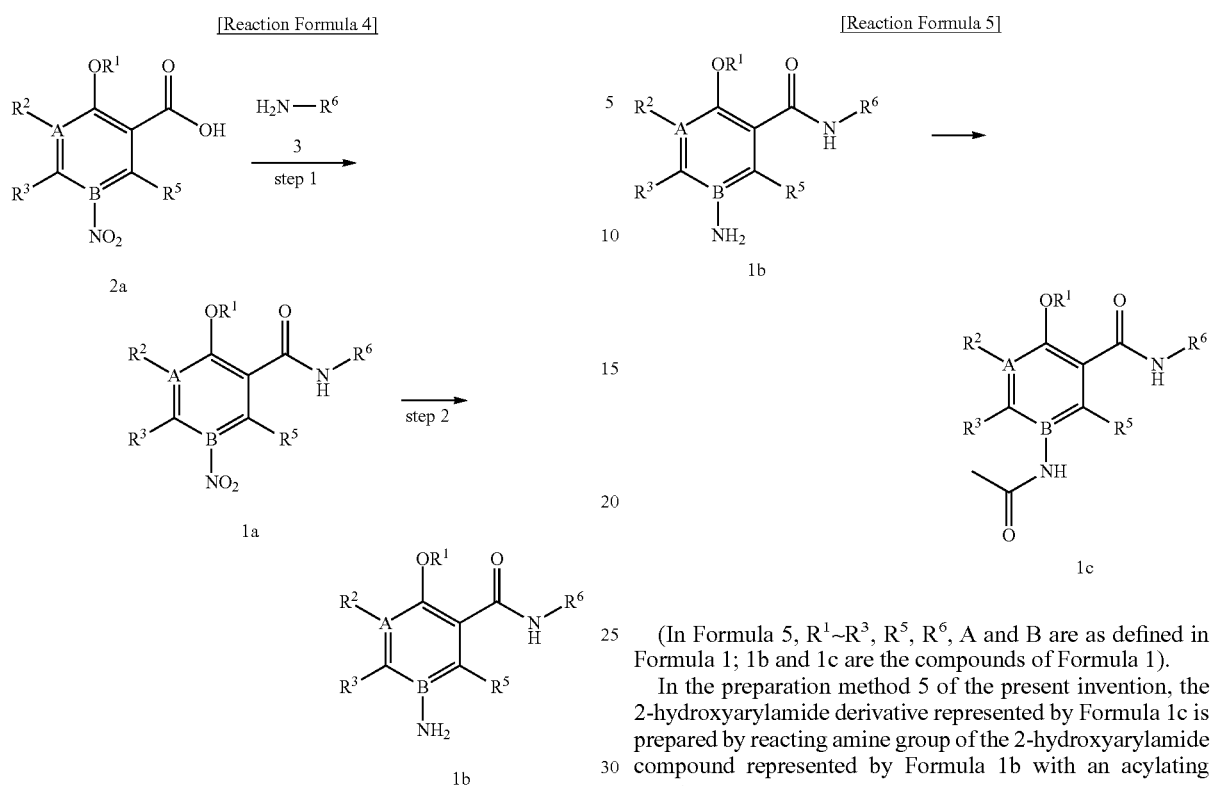

(In Formula 4, $R^1$~$R^3$, $R^5$, $R^6$, A and B are as defined in Formula 1; 1a and 1b are the compounds of Formula 1; 2a is the compound of Formula 1).

In the preparation method 4 of the present invention, the 2-hydroxyarylamide derivative represented by Formula 1a is prepared as follows: the 2-hydroxyaryl acid compound represented by Formula 2a is dissolved in an organic solvent in the presence of argon gas; a chlorinating agent is added thereto in the presence of a base; the amine compound represented by Formula 3 is added thereto; and the mixture is reflux-stirred to give the 2-hydroxyarylamide derivative represented by Formula 1a.

At this time, the conditions for the coupling reaction of step 1 are as described in the preparation method 2.

In step 2, the compound represented by Formula 1b is prepared by reducing the compound represented by Formula 1a prepared in step 1 using a reducing agent. More precisely, nitro group of the compound represented by Formula 1a is reduced to amine group of the compound represented by Formula 1b in this step.

At this time, the usable reducing agent herein is ammonium chloride ($NH_4Cl$) or hydrogen ($H_2$) gas, and preferably ammonium chloride ($NH_4Cl$).

The acceptable catalyst for the above reduction is iron powder, Pd/C, $Pd(OAc)_2$, or $PtO_2$, and preferably iron powder.

The usable organic solvent herein can be methanol, ethanol, isopropanol, tetrahydrofurane, distilled water, or a mixed solvent thereof, which has no effect on the reaction, and preferably isopropanol.

Preparation Method 5

The preparation method of the derivative of Formula of the present invention, as shown in the below Reaction Formula 5, includes the step of preparing the compound represented by Formula 1c through acylation of the compound represented by Formula 1b:

(In Formula 5, $R^1$~$R^3$, $R^5$, $R^6$, A and B are as defined in Formula 1; 1b and 1c are the compounds of Formula 1).

In the preparation method 5 of the present invention, the 2-hydroxyarylamide derivative represented by Formula 1c is prepared by reacting amine group of the 2-hydroxyarylamide compound represented by Formula 1b with an acylating agent.

The acylating agent herein is acetic anhydride or acetyl chloride, and preferably acetic anhydride.

The usable organic solvent herein can be acetic acid which does not affect the reaction.

The present invention also provides a pharmaceutical composition for preventing or treating cancer comprising the 2-hydroxyarylamide derivative represented by Formula 1 or the pharmaceutically acceptable salt thereof as an active ingredient.

The cancer herein includes colorectal cancer, lung cancer, breast cancer, prostate cancer, ovarian cancer, pancreatic cancer, and stomach cancer.

The 2-hydroxyarylamide derivative represented by Formula 1 of the present invention was confirmed by the investigation of TMPRSS4 serine protease activity using peptide substrate to inhibit the activity of TMPRSS4 serine protease dose-dependently. In particular, the compounds of Examples 1, 2, 4, 6, 8, 9, 16, 21-23, 26, 32, 33, 36, 39, 65, 66, 70, 71, 73, 75 demonstrated 51~100% inhibitory effect at the concentration of 10 μM (see Experimental Example 1 and Table 2).

The inhibitory effect on the infiltration of colorectal cancer cells expressing TMPRSS4 was investigated. As a result, the compounds of Examples 1, 8, 19, 22, 25, 27, 28, 32, 33, 36, 37, 53, 55 and 65 were confirmed to inhibit the infiltration up to 26~81%. In particular, the compound of Example 19 inhibited 81% of the infiltration (see Experimental Example 2 and Table 3).

Therefore, it was confirmed that the compound of the present invention is excellent in the inhibition of the activity of TMPRSS4 serine protease and the suppression of the infiltration of TMPRSS4-expressed cancer cells, and thus can be useful as a composition for preventing or treating cancer by inhibiting TMPRSS4 over-expressed in cancer cells, particularly, colorectal cancer, lung cancer, breast cancer, prostate cancer, ovarian cancer, pancreatic cancer, or stomach cancer cells.

The present invention also provides a pharmaceutical composition for inhibiting TMPRSS4 (transmembrane protease serine-4) which comprises the 2-hydroxyarylamide derivative represented by the above Formula 1 or the pharmaceutically acceptable salt thereof as an active ingredient.

The present invention also provides a pharmaceutical composition for suppressing cancer metastasis which comprises the 2-hydroxyarylamide derivative represented by the above Formula 1 or the pharmaceutically acceptable salt thereof as an active ingredient.

The 2-hydroxyarylamide derivative represented by Formula 1 of the present invention has excellent effect of inhibiting the activity of TMPRSS4 serine protease which is an important mediator for infiltration, metastasis, migration, and adhesion as well as EMP (epithelial mesenchymal transition) in human epithelial cancer cells. That is, the derivative of the present invention is excellent in inhibiting cancer cell infiltration and metastasis particularly induced by TMPRSS4 serine protease (see Experimental Examples 1 and 2).

The pharmaceutical composition comprising the 2-hydroxyarylamide derivative represented by the above Formula 1 or the pharmaceutically acceptable salt thereof as an active ingredient of the present invention can be administered orally or parenterally and be used in general forms of pharmaceutical formulation, but not always limited thereto.

The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

The pharmaceutical composition comprising the 2-hydroxyarylamide derivative represented by Formula 1 as an active ingredient of the present invention can be administered by parenterally and the parenteral administration includes subcutaneous injection, intravenous injection, intramuscular injection and intrathoracic injection.

To prepare the pharmaceutical composition of the present invention as a formulation for parenteral administration, the 2-hydroxyarylamide derivative represented by Formula 1 or the pharmaceutically acceptable salt thereof is mixed with a stabilizer or a buffering agent to produce a solution or suspension, which is then formulated as ampoules or vials. The composition can be sterilized and/or can additionally include preservatives, resolvents, stabilizers, wetting agents, emulsifiers, sweetening agents, pigments, flavoring agents, osmosis controlling salts, buffering agents, coating agents, or antioxidants. The composition can also include other therapeutically valuable additives. The composition can be formulated by the conventional method such as mixing, granulation, or coating.

The effective dosage of the pharmaceutical composition comprising the 2-hydroxyarylamide derivative represented by Formula 1 as an active ingredient of the present invention can be determined according to age, weight, gender, administration method, health condition, and severity of disease. The preferable dosage is 0.01~200 mg/kg per day, which can be administered orally or parenterally several times a day or preferably 1~3 times a day according to the decision of a doctor or a pharmacist.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Preparation of N-(3,5-bis(trifluoromethyl)phenyl)-5-chloro-2-hydroxybenzamide

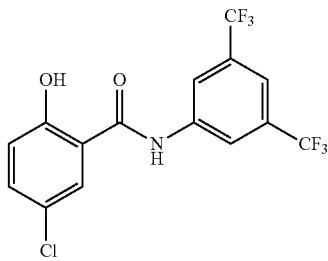

To 30 ml of toluene were added 5-chlorosalicylic acid (862 mg, 5 mmol), 3,5-bis(trifluoromethyl)aniline (1.37 g, 6 mmol), and phosphoroustrichloride (755 mg, 5.5 mmol) in the presence of argon gas, followed by stirring for 6 hours through heat-reflux. Sodium hydrogen carbonate was added to the mixture to adjust pH to 7, followed by concentration under reduced pressure. The mixture was dissolved in 60 ml of ethylacetate, which was washed with water (40 ml×2). The organic layer was concentrated under reduced pressure, followed by column chromatography to give 1.09 g of the target compound (yield: 57%).

m.p: 172-173° C.;
$^1$H-NMR (300 MHz, DMSO-d$^6$): δ 7.05 (1H, d, J=8.7 Hz), 7.49 (1H, dd, J=8.7, 2.7 Hz), 7.85 (1H, s), 7.87 (1H, d, J=2.7 Hz), 8.45 (2H, s), 10.85 (1H, s), 11.39 (1H, s).

EXAMPLE 2

Preparation of N-(3,5-bis(trifluoromethyl)phenyl)3,5-dichloro-2-hydroxybenzamide

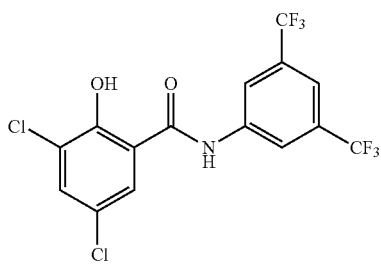 [SMILES: O=C(Nc1cc(C(F)(F)F)cc(C(F)(F)F)c1)c1cc(Cl)cc(Cl)c1O]

550 mg of the target compound (yield: 26%) was obtained by the same manner as described in Example 1 except that 3,5-dichloro-2-hydroxybenzoic acid was used instead of 5-chlorosalicylic acid.

m.p: 141-143° C.;

¹H-NMR (300 MHz, DMSO-d⁶) δ 7.84 (s, 1H), 8.00 (s, 1H), 8.01 (s, 1H), 8.41 (s, 2H), 11.13 (s, 1H).

EXAMPLE 3

Preparation of N-(3,5-bis(trifluoromethyl)phenyl)-2-hydroxy-5-methylbenzamide

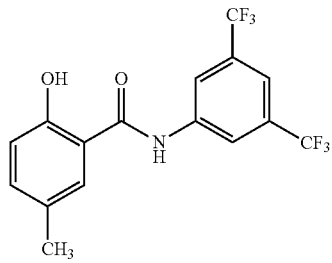 [SMILES: Cc1ccc(O)c(C(=O)Nc2cc(C(F)(F)F)cc(C(F)(F)F)c2)c1]

400 mg of the target compound (yield: 22%) was obtained by the same manner as described in Example 1 except that 2-hydroxy-5-methylbenzoic acid was used instead of 5-chlorosalicylic acid.
m.p: 145-147° C.;
¹H-NMR (300 MHz, DMSO-D⁶) δ 2.28 (s, 3H), 6.90 (d, J=5.0 Hz, 1H), 7.26 (dd, J=2.3, 2.0 Hz, 1H), 7.69 (s, 1H), 7.83 (s, 1H), 8.46 (s, 2H), 10.81 (s, 1H), 10.86 (s, 1H).

EXAMPLE 4

Preparation of 5-chloro-N-(4-fluoro-3-(trifluoromethyl)phenyl)-2-hydroxybenzamide

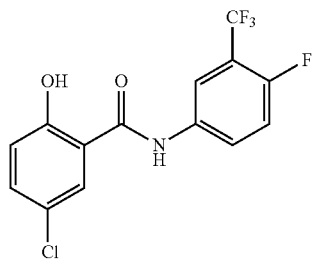 [SMILES: O=C(Nc1ccc(F)c(C(F)(F)F)c1)c1cc(Cl)ccc1O]

982 mg of the target compound (yield: 59%) was obtained by the same manner as described in Example 1 except that 4-fluoro-3-(trifluoromethyl)aniline was used instead of 3,5-bis(trifluoromethyl)aniline.
m.p: 203-205° C.;
¹H-NMR (300 MHz, DMSO-d⁶) δ 7.02 (d, J=8.8 Hz, 1H) 7.56-7.45 (m, 2H), 7.46-7.57 (m, 1H), 8.02-7.98 (m, 1H), 8.19 (dd, J=2.1, 2.0 Hz, 1H), 10.62 (s, 1H), 11.55 (s, 1H).

EXAMPLE 5

Preparation of N-(3,5-bis(trifluoromethyl)phenyl)-2-hydroxybenzamide

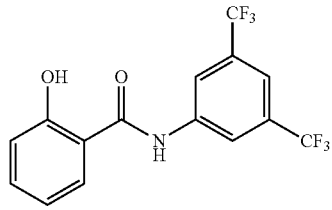 [SMILES: O=C(Nc1cc(C(F)(F)F)cc(C(F)(F)F)c1)c1ccccc1O]

594 mg of the target compound (yield: 34%) was obtained by the same manner as described in Example 1 except that 2-hydroxybenzoic acid was used instead of 5-chlorosalicylic acid.
m.p: 181-182° C.;
¹H-NMR (300 MHz, DMSO-d⁶) δ 7.02-6.96 (m, 2H), 7.48-7.42 (m, 1H), 7.87-7.83 (m, 2H), 8.46 (s, 2H), 10.85 (s, 1H).

EXAMPLE 6

Preparation of 5-chloro-2-hydroxy-N-(3-methoxy-5-(trifluoromethyl)phenyl)benzamide

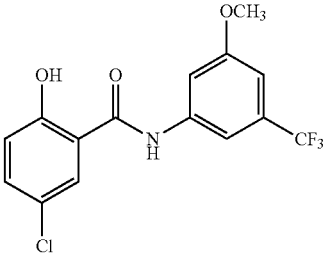 [SMILES: COc1cc(NC(=O)c2cc(Cl)ccc2O)cc(C(F)(F)F)c1]

847 mg of the target compound (yield: 49%) was obtained by the same manner as described in Example 1 except that 3-methoxy-5-(trifluoromethyl)aniline was used instead of 3,5-bis(trifluoromethyl)aniline.
m.p: 191-192° C.;
¹H-NMR (300 MHz, DMSO-d⁶) δ 3.84 (s, 3H) 7.01-7.04 (m, 2H) 7.47 (dd, J=8.8, 2.6 Hz, 1H), 7.60 (s, 1H), 7.76 (s, 1H), 7.88 (d, J=2.6 Hz, 1H), 10.57 (s, 1H), 11.53 (s, 1H).

EXAMPLE 7

Preparation of N-(3,5-bis(trifluoromethyl)phenyl)-2-hydroxy-5-methoxybenzamide

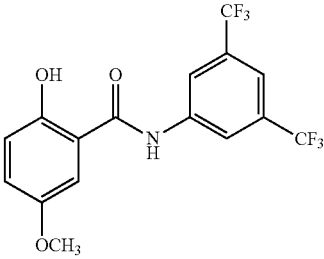

986 mg of the target compound (yield: 52%) was obtained by the same manner as described in Example 1 except that 2-hydroxy-5-methoxybenzoic acid was used instead of 5-chlorosalicylic acid.
m.p: 208-210° C.;
¹H-NMR (300 MHz, DMSO-d⁶) δ 6.96-6.94 (d, J=8.9 Hz, 1H), 3.75 (s, 3H), 7.06-7.10 (dd, J=8.9, 3.1 Hz, 1H), 7.42 (d, J=3.0 Hz, 1H), 7.81 (s, 1H), 8.45 (s, 2H), 10.83 (s, 1H), 10.95 (s, 1H).

EXAMPLE 8

Preparation of N-(3,5-bis(trifluoromethyl)phenyl)-2-hydroxy-3-naphthaamide

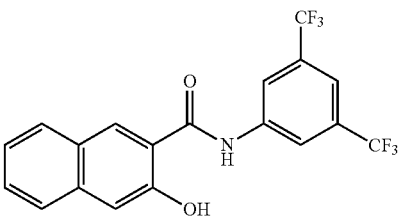 [SMILES: O=C(Nc1cc(C(F)(F)F)cc(C(F)(F)F)c1)c1cc2ccccc2cc1O]

340 mg of the target compound (yield: 17%) was obtained by the same manner as described in Example 1 except that 3-hydroxy-2-naphthoic acid was used instead of 5-chlorosalicylic acid.

m.p: 226-229° C.;

$^1$H-NMR (300 MHz, DMSO-d$^6$) δ 7.34-7.38 (m, 2H), 7.49-7.53 (m, 1H), 7.77 (d, J=7.8 Hz, 1H), 7.84 (s, 1H), 7.92 (d, J=7.7 Hz, 1H), 8.40 (s, 1H), 8.50 (s, 2H), 10.99 (s, 1H).

EXAMPLE 9

Preparation of N-(3,5-bis(trifluoromethyl)phenyl)-5-bromo-2-hydroxybenzamide

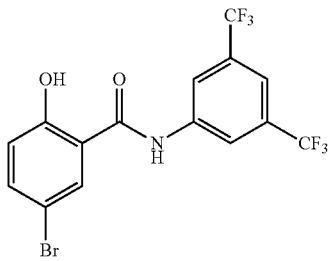 [SMILES: O=C(Nc1cc(C(F)(F)F)cc(C(F)(F)F)c1)c1cc(Br)ccc1O]

340 mg of the target compound (yield: 17%) was obtained by the same manner as described in Example 1 except that 2-hydroxy-5-bromobenzoic acid was used instead of 5-chlorosalicylic acid.

m.p: 194-195° C.;

$^1$H-NMR (300 MHz, DMSO-d$^6$) δ 6.98 (d, J=8.3 Hz, 1H), 7.60 (dd, J=8.8, 2.6 Hz, 1H), 7.84 (s, 1H), 7.97 (d, J=2.5 Hz, 1H), 8.44 (s, 2H), 10.85 (s, 1H), 11.41 (s, 1H).

EXAMPLE 10

Preparation of 5-chloro-N-(3-(trifluoromethyl)phenyl)-2-hydroxybenzamide

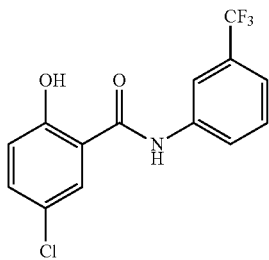 [SMILES: O=C(Nc1cccc(C(F)(F)F)c1)c1cc(Cl)ccc1O]

805 mg of the target compound (yield: 51%) was obtained by the same manner as described in Example 1 except that 3-(trifluoromethyl)aniline was used instead of 3,5-bis(trifluoromethyl)aniline.

m.p: 181-182° C.;

$^1$H-NMR (300 MHz, DMSO-d$^6$) δ 7.02 (d, J=8.8 Hz, 1H), 7.45-7.50 (m, 2H), 7.61 (dd, J=8.0, 8.0 Hz, 1H), 7.89 (d, J=2.6 Hz, 1H), 7.94 (d, J=8.3 Hz, 1H), 8.20 (s, 1H), 10.63 (s, 1H), 11.57 (s, 1H).

EXAMPLE 11

Preparation of 5-chloro-N-(3-cyanophenyl)-2-hydroxybenzamide

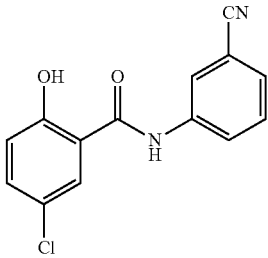

286 mg of the target compound (yield: 21%) was obtained by the same manner as described in Example 1 except that 3-(cyano)aniline was used instead of 3,5-bis(trifluoromethyl)aniline.

m.p: 240-241° C.;

$^1$H-NMR (300 MHz, DMSO-d$^6$) δ 7.02 (d, J=8.8 Hz, 1H), 7.45-7.49 (dd, J=8.8, 2.6 Hz, 1H), 7.55-7.61 (m, 2H), 7.86 (d, J=2.6 Hz, 1H), 7.95-7.99 (m, 1H), 8.20 (s, 1H), 10.62 (s, 1H), 11.56 (s, 1H).

EXAMPLE 12

Preparation of 5-chloro-N-(4-cyanophenyl)-2-hydroxybenzamide

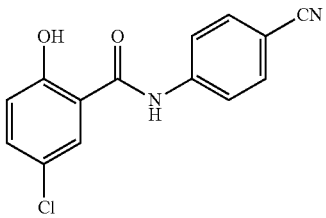 [SMILES: N#Cc1ccc(NC(=O)c2cc(Cl)ccc2O)cc1]

96 mg of the target compound (yield: 7%) was obtained by the same manner as described in Example 1 except that 4-(cyano)aniline was used instead of 3,5-bis(trifluoromethyl)aniline.

m.p: 246-247° C.;

$^1$H-NMR (300 MHz, DMSO-d$^6$) δ 7.00 (d, J=8.8 Hz, 1H), 7.43-7.47 (dd, J=8.8, 2.6 Hz, 1H), 7.81-7.84 (m, 3H), 7.91 (d, J=8.7 Hz, 2H), 10.82 (s, 1H).

EXAMPLE 13

Preparation of N-(3,5-bis(trifluoromethyl)phenyl)-4-(trifluoromethyl)-2-hydroxybenzamide

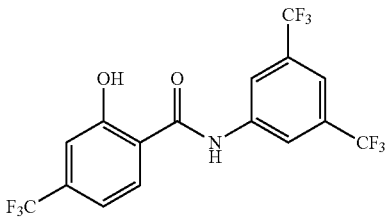 [SMILES: O=C(Nc1cc(C(F)(F)F)cc(C(F)(F)F)c1)c1ccc(C(F)(F)F)cc1O]

647 mg of the target compound (yield: 31%) was obtained by the same manner as described in Example 1 except that 3-trifluoromethyl-2-hydroxybenzoic acid was used instead of 5-chlorosalicylic acid.

$^1$H-NMR (300 MHz, DMSO-d$^6$) δ 7.30 (d, J=7.7 Hz, 2H), 7.85 (s, 1H), 7.92 (d, J=8.0 Hz, 1H), 8.44 (s, 2H), 10.94 (s, 1H), 11.48 (s, 1H).

EXAMPLE 14

Preparation of N-(3,5-bis(trifluoromethyl)phenyl)-5-fluoro-2-hydroxybenzamide

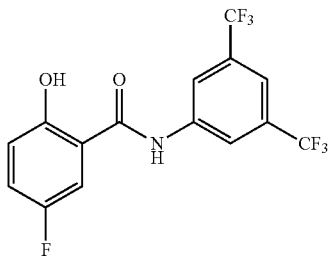 [SMILES: O=C(Nc1cc(C(F)(F)F)cc(C(F)(F)F)c1)c1cc(F)ccc1O]

881 mg of the target compound (yield: 48%) was obtained by the same manner as described in Example 1 except that 3-fluoro-2-hydroxybenzoic acid was used instead of 5-chlorosalicylic acid.

m.p: 187-178° C.;
$^1$H-NMR (300 MHz, DMSO-d$^6$) δ 7.01-7.05 (dd, J=9.0, 4.6 Hz, 1H), 7.29-7.36 (m, 1H), 7.63-7.67 (dd, J=9.4, 3.2 Hz, 1H), 7.84 (s, 1H), 8.45 (s, 1H), 10.82 (s, 1H), 11.21 (s, 1H).

EXAMPLE 15

Preparation of 5-chloro-N-(4-(trifluoromethyl)phenyl)-2-hydroxybenzamide

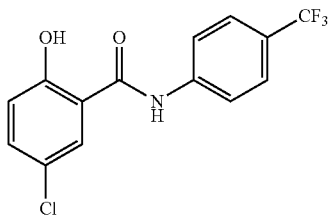 [SMILES: O=C(Nc1ccc(C(F)(F)F)cc1)c1cc(Cl)ccc1O]

286 mg of the target compound (yield: 21%) was obtained by the same manner as described in Example 1 except that 4-(trifluoromethyl)aniline was used instead of 3,5-bis(trifluoromethyl)aniline.

m.p: 222-223° C.;
$^1$H-NMR (300 MHz, DMSO-d$^6$) δ 7.02 (d, J=8.8 Hz, 1H), 7.45-7.49 (dd, J=8.8, 2.7 Hz, 1H), 7.74 (d, J=8.6 Hz, 2H), 7.88 (d, J=2.6 Hz, 1H), 7.94 (d, J=8.5 Hz, 1H), 10.65 (s, 1H), 11.56 (s, 1H).

EXAMPLE 16

Preparation of N-(4-bromo-3-(trifluoromethyl)phenyl)-5-chloro-2-hydroxybenzamine

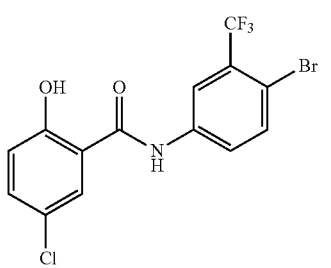 [SMILES: O=C(Nc1ccc(Br)c(C(F)(F)F)c1)c1cc(Cl)ccc1O]

513 mg of the target compound (yield: 26%) was obtained by the same manner as described in Example 1 except that 4-bromo-3-(trifluoromethyl)aniline was used instead of 3,5-bis(trifluoromethyl)aniline.

$^1$H-NMR (300 MHz, DMSO-d$^6$) δ 7.02 (d, J=8.8 Hz, 1H), 7.44-7.48 (dd, J=8.8, 2.6 Hz, 1H), 7.85-7.93 (m, 3H), 8.29 (s, 1H), 10.65 (s, 1H), 11.53 (s, 1H).

EXAMPLE 17

Preparation of 5-chloro-N-(3-(trifluoromethyl)-2-methylphenyl)-2-hydroxybenzamide

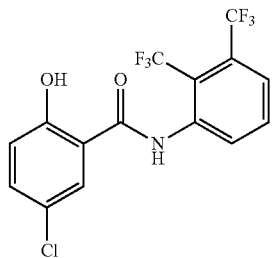 [SMILES: O=C(Nc1cccc(C(F)(F)F)c1C(F)(F)F)c1cc(Cl)ccc1O]

594 mg of the target compound (yield: 36%) was obtained by the same manner as described in Example 1 except that 2,3-bis(trifluoromethyl)aniline was used instead of 3,5-bis(trifluoromethyl)aniline.

m.p: 163-164° C.;
$^1$H-NMR (300 MHz, DMSO-d$^6$) δ 2.37 (s, 3H), 7.04 (d, J=8.8 Hz, 1H), 7.42-7.51 (m, 2H), 7.59 (d, J=7.6 Hz, 1H), 7.97-8.01 (m, 2H), 10.44 (s, 1H), 12.09 (s, 1H).

EXAMPLE 18

Preparation of N-(2,5-bis(trifluoromethyl)phenyl)-5-chloro-2-hydroxybenzamine

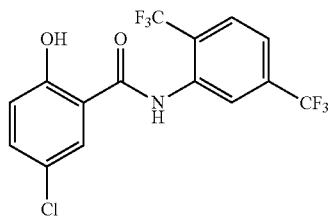

556 mg of the target compound (yield: 29%) was obtained by the same manner as described in Example 1 except that 2,5-bis(trifluoro)aniline was used instead of 3,5-bis(trifluoromethyl)aniline.

m.p: 202-203° C.;
$^1$H-NMR (300 MHz, DMSO-d$^6$) δ 7.06 (d, J=8.8 Hz, 1H), 7.51-7.55 (dd, J=8.8, 2.8 Hz, 1H), 7.75 (d, J=8.3 Hz, 1H), 7.97 (d, J=2.8 Hz, 1H), 8.03 (s, 1H), 8.73 (s, 1H), 11.04 (s, 1H), 12.36 (s, 1H).

EXAMPLE 19

Preparation of 5-chloro-N-(4-cyano-3-(trifluoromethyl)phenyl)-2-hydroxybenzamide

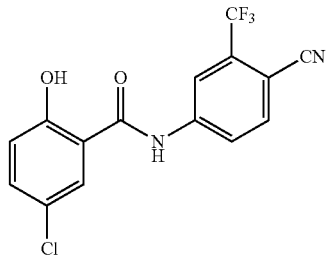 [SMILES: N#Cc1ccc(NC(=O)c2cc(Cl)ccc2O)cc1C(F)(F)F]

273 mg of the target compound (yield: 16%) was obtained by the same manner as described in Example 1 except that 3-(trifluoromethyl)-4-(cyano)aniline was used instead of 3,5-bis(trifluoromethyl)aniline.

m.p: 214-215° C.;

$^1$H-NMR (300 MHz, DMSO-d$^6$) δ 7.03 (d, J=8.8 Hz, 1H), 7.46-7.50 (dd, J=8.8, 2.6 Hz, 1H), 7.79 (d, J=2.6 Hz, 1H), 8.15 (s, 2H), 8.42 (s, 1H), 10.97 (s, 1H), 11.34 (s, 1H).

EXAMPLE 20

Preparation of N-(2-bromo-5-(trifluoromethyl)phenyl)-5-chloro-2-hydroxybenzamide

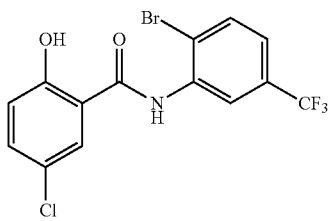 [SMILES: O=C(Nc1cc(C(F)(F)F)ccc1Br)c1cc(Cl)ccc1O]

868 mg of the target compound (yield: 44%) was obtained by the same manner as described in Example 1 except that 2-(bromo)-5-(trifluoro)aniline was used instead of 3,5-bis(trifluoromethyl)aniline.

m.p: 174-175° C.;

$^1$H-NMR (300 MHz, DMSO-d$^6$) δ 7.09 (d, J=8.8 Hz, 1H), 7.44-7.53 (m, 2H), 7.95-7.97 (m, 2H), 8.80 (s, 1H), 11.02 (s, 1H), 12.37 (s, 1H).

EXAMPLE 21

Preparation of 5-chloro-N-(2-fluoro-5-(trifluoromethyl)phenyl)-2-hydroxybenzamide

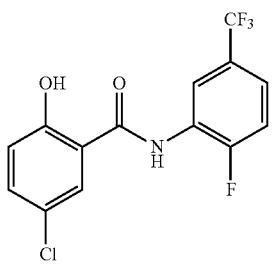 [SMILES: O=C(Nc1cc(C(F)(F)F)ccc1F)c1cc(Cl)ccc1O]

634 mg of the target compound (yield: 38%) was obtained by the same manner as described in Example 1 except that 3-(trifluoromethyl)-6-(fluoro)aniline was used instead of 3,5-bis(trifluoromethyl)aniline.

m.p: 199-200° C.;

$^1$H-NMR (300 MHz, DMSO-d$^6$) δ 7.06 (d, J=8.8 Hz, 1H), 7.49-7.53 (m, 1H), 7.59 (d, J=8.1 Hz, 2H), 7.94 (d, J=2.8 Hz, 1H), 8.72 (s, 1H), 10.91 (s, 1H), 12.25 (s, 1H).

EXAMPLE 22

Preparation of N-(3-bromo-5-(trifluoromethyl)phenyl)-5-chloro-2-hydroxybenzamide

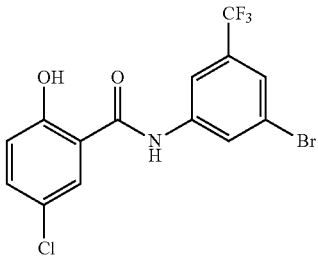 [SMILES: O=C(Nc1cc(Br)cc(C(F)(F)F)c1)c1cc(Cl)ccc1O]

1010 mg of the target compound (yield: 51%) was obtained by the same manner as described in Example 1 except that 3-(trifluoromethyl)-5-(bromo)aniline was used instead of 3,5-bis(trifluoromethyl)aniline.

m.p: 200-202° C.;

$^1$H-NMR (300 MHz, DMSO-d$^6$) δ 7.03 (d, J=8.8 Hz, 1H), 7.46-7.49 (dd, J=8.8, 2.6 Hz, 1H), 7.71 (s, 1H), 7.84 (d, J=2.6 Hz, 1H), 8.15 (s, 1H), 8.27 (s, 1H), 10.72 (s, 1H), 11.45 (s, 1H).

EXAMPLE 23

Preparation of 5-chloro-N-(2-chloro-5-(trifluoromethyl)phenyl)-2-hydroxybenzamide

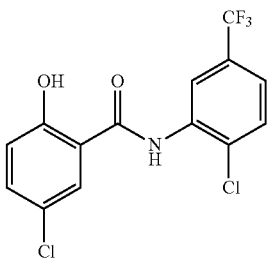

1400 mg of the target compound (yield: 80%) was obtained by the same manner as described in Example 1 except that 3-(trifluoromethyl)-6-(chloro)aniline was used instead of 3,5-bis(trifluoromethyl)aniline.

m.p: 180-182° C.;

$^1$H-NMR (300 MHz, DMSO-d$^6$) δ 7.08 (d, J=8.8 Hz, 1H), 7.50-7.56 (m, 2H), 7.82 (d, J=8.4 Hz, 1H), 7.97 (d, J=2.8 Hz, 1H), 8.87 (d, J=2.0 Hz, 1H), 11.19 (s, 1H), 12.43 (s, 1H).

EXAMPLE 24

Preparation of N-(3,5-bis-trifluoromethyl-benzyl)-5-chloro-2-hydroxy-benzamide

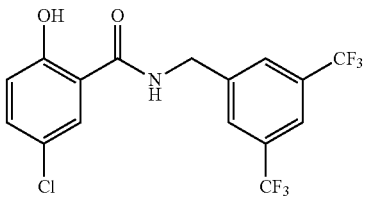 [SMILES: O=C(NCc1cc(C(F)(F)F)cc(C(F)(F)F)c1)c1cc(Cl)ccc1O]

To 12 ml of dichloromethane were added 5-chlorosalicylic acid (690 mg, 4 mmol), 3,5-bis(trifluoromethyl)aniline (972 mg, 4 mmol), EDCI (1.2 g, 8 mmol), and DMAP (49 mg, 0.4 mmol) in the presence of argon gas, followed by stirring for 12 hours at room temperature. The mixture was concentrated under reduced pressure, and then dissolved in 60 ml of ethylacetate, which was washed with water (40 ml×2). The organic layer was concentrated under reduced pressure, followed by column chromatography (developing solvent: hexane/ethylacetate=1/10) to give 609 mg of the target compound (yield: 38%).

m.p: 125-127° C.;

$^{1}$H-NMR (300 MHz, DMSO-d$^{6}$) δ 4.68 (d, J=5.8 Hz, 2H), 6.97 (d, J=8.8 Hz, 1H), 7.44 (dd, J=8.8, 2.6 Hz, 1H), 7.89 (d, J=2.7 Hz, 1H), 8.03 (d, J=10.9 Hz, 3H), 9.41 (t, J=5.8 Hz, 1H), 12.09 (s, 1H).

EXAMPLE 25

Preparation of 5-chloro-2-hydroxy-N-quinoline-3-yl-benzamide

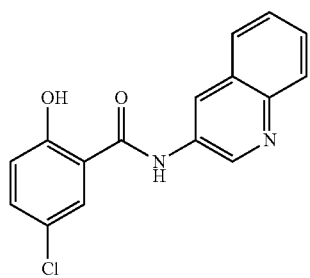 [SMILES: O=C(Nc1cnc2ccccc2c1)c1cc(Cl)ccc1O]

104 mg of the target compound (yield: 7%) was obtained by the same manner as described in Example 1 except that quinoline-3-amine was used instead of 3,5-bis(trifluoromethyl)aniline.

m.p: 253-255° C.;

$^{1}$H-NMR (300 MHz, DMSO-d$^{6}$) δ 7.05-7.12 (m, 1H), 7.46-7.67 (m, 3H), 7.98 (dd J=6.6 Hz, 3H), 8.79 (s, 1H), 9.04 (s, 1H), 10.77 (s, 1H), 11.73 (s, br, 1H).

EXAMPLE 26

Preparation of N-(3,5-bis-trifluoromethyl-phenyl)-3-chloro-2-hydroxy-benzamide

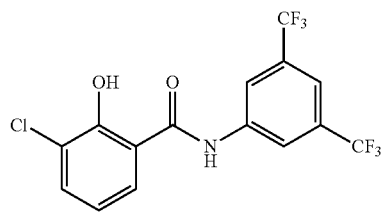 [SMILES: O=C(Nc1cc(C(F)(F)F)cc(C(F)(F)F)c1)c1cccc(Cl)c1O]

1.13 mg of the target compound (yield: 59%) was obtained by the same manner as described in Example 1 except that 3-chloro-2-hydroxybenzoic acid was used instead of 5-chlorosalicylic acid.

m.p: 156-157° C.;

$^{1}$H-NMR (300 MHz, DMSO-d$^{6}$) δ 7.00-7.07 (m, 1H), 7.66-7.71 (m, 1H), 7.88-7.94 (m, 2H), 8.44 (d, J=3.4 Hz, 2H), 11.02 (s, 1H), 11.94 (s, br, 1H).

EXAMPLE 27

Preparation of 5-chloro-N-(2-chloro-4-cyano-phenyl)-2-hydroxy-benzamide

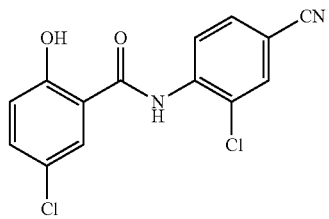 [SMILES: N#Cc1ccc(NC(=O)c2cc(Cl)ccc2O)c(Cl)c1]

415 mg of the target compound (yield: 27%) was obtained by the same manner as described in Example 1 except that 4-(cyano)-3-(chloro)aniline was used instead of 3,5-bis(trifluoromethyl)aniline.

$^{1}$H-NMR (300 MHz, DMSO-d$^{6}$) δ 7.08 (d, J=8.8 Hz, 1H), 7.52 (dd, J=8.8, 2.8 Hz, 1H), 7.87 (dd, J=8.7, 2.0 Hz, 1H), 7.95 (d, J=2.8 Hz, 1H), 8.17 (d, J=1.8 Hz, 1H), 8.70 (d, J=8.7 Hz, 1H), 11.24 (s, 1H), 12.42 (s, br, 1H).

EXAMPLE 28

Preparation of 5-chloro-2-hydroxy-N-(5-trifluoromethyl-[1,3,4]thiadiazole-2-yl)-benzamide

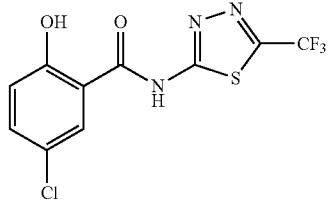 [SMILES: O=C(Nc1nnc(C(F)(F)F)s1)c1cc(Cl)ccc1O]

728 mg of the target compound (yield: 45%) was obtained by the same manner as described in Example 1 except that 5-(trifluoromethyl)-1,3,4-thiadiazole-2-amine was used instead of 3,5-bis(trifluoromethyl)aniline.

$^{1}$H-NMR (300 MHz, DMSO-d$^{6}$) δ 6.96 (d, J=8.8 Hz, 1H), 7.42 (dd, J=8.8, 2.8 Hz, 1H), 7.83 (d, J=2.8 Hz, 1H).

EXAMPLE 29

Preparation of 5-chloro-N-(2-chloro-3,5-bis-trifluoromethyl-phenyl)-2-hydroxy-benzamide

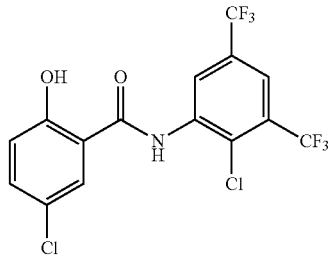 [SMILES: O=C(Nc1cc(C(F)(F)F)cc(C(F)(F)F)c1Cl)c1cc(Cl)ccc1O]

878 mg of the target compound (yield: 42%) was obtained by the same manner as described in Example 1 except that 3,5-bis(trifluoromethyl)-6-(chloro)aniline was used instead of 3,5-bis(trifluoromethyl)aniline.

¹H-NMR (300 MHz, DMSO-d⁶) δ7.09 (d, J=8.7 Hz, 1H), 7.53 (dd, J=8.8, 2.8 Hz, 1H), 7.93 (s, 1H), 7.95 (d, J=2.8 Hz, 1H), 9.14 (s, 1H), 11.31 (s, 1H), 12.45 (s, 1H).

EXAMPLE 30

Preparation of N-(2-chloro-3,5-bis(trifluoromethyl)phenyl)-4',6'-difluoro-4-hydroxybiphenyl-3-carboxamide

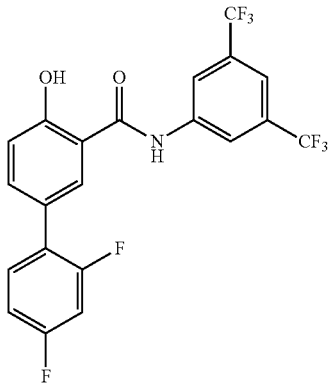 [SMILES: O=C(Nc1cc(C(F)(F)F)cc(C(F)(F)F)c1)c1cc(-c2ccc(F)cc2F)ccc1O]

1360 mg of the target compound (yield: 59%) was obtained by the same manner as described in Example 1 except that 4',6'-difluoro-4-hydroxybiphenyl-3-carboxylic acid was used instead of 5-chlorosalicylic acid.

¹H-NMR (300 MHz, DMSO-d⁶) δ 7.13 (d, J=8.6 Hz, 1H), 7.20-7.25 (m, 1H), 7.35-7.42 (m, 1H), 7.57-7.65 (m, 2H), 7.85 (s, 1H), 8.02 (s, 1H), 8.48 (s, 2H), 10.90 (s, 1H), 11.47 (s, 1H).

EXAMPLE 31

Preparation of 5-amino-N-(3,5-bis(trifluoromethyl)phenyl)-2-hydroxybenzamide

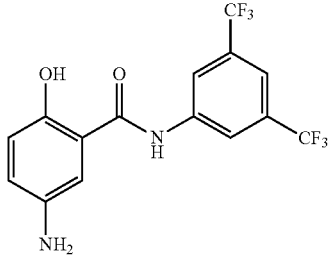

Step 1: Preparation of N-(3,5-bis-trifluoromethyl-phenyl)-2-hydroxy-5-nitro-benzamide 517 mg of the target compound (yield: 26%) was obtained by the same manner as described in Example 1 except that 2-hydroxy-5-nitrobenzoic acid was used instead of 5-chlorosalicylic acid.

¹H-NMR (300 MHz, DMSO-d⁶) δ 7.17 (d, J=8.9 Hz, 1H), 7.87 (s, 1H), 8.30 (d, J=9.1 Hz, 1H), 8.45 (s, 2H), 8.69 (s, 1H), 11.13 (s, 1H).

Step 2: Preparation of 5-amino-N-(3,5-bis(trifluoromethyl)phenyl)-2-hydroxybenzamide N-(3,5-bis-trifluoromethyl-phenyl)-2-hydroxy-5-nitro-benzamide (400 mg, 1.4 mmol) prepared in step 1 was dissolved in 4.2 . of isopropanol (IPA), to which 3 g of iron powder and 3 . of NH₄Cl saturated solution were added.

The mixture was stirred for 3 hours. The reaction mixture was filtered by using silica gel and celite. The filtered solution was concentrated under reduced pressure. The obtained residue was purified by silica gel column chromatography (hexane:ethylacetate=5:1) to give 280 mg of the target compound (yield: 77%).

¹H-NMR (300 MHz, DMSO-d⁶) δ 4.79 (s, 2H), 6.76 (d, J=8.0 Hz, 2H), 7.08 (s, 1H), 7.79 (s, 1H), 8.44 (s, 2H), 10.37 (s, 1H), 10.82 (s, 1H).

EXAMPLE 32

Preparation of 5-chloro-N-(4-chloro-3-(trifluoromethyl)phenyl)-2-hydroxybenzamide

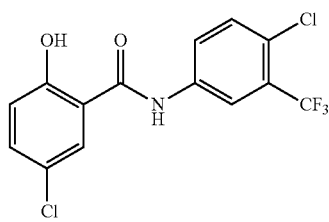

655 mg of the target compound (yield: 38%) was obtained by the same manner as described in Example 1 except that 3-(chloro)-4-(trifluoromethyl)aniline was used instead of 3,5-bis(trifluoromethyl)aniline.

m.p: 230-232° C.;

¹H-NMR (300 MHz, DMSO-d⁶) δ 7.02 (d, J=8.7 Hz, 1H), 7.46 (d, J=7.5 Hz, 1H), 7.72 (d, J=9.0 Hz, 1H), 7.85 (s, 1H), 7.99 (d, J=8.4 Hz, 1H), 8.30 (s, 1H), 10.68 (s, 1H).

EXAMPLE 33

Preparation of 5-chloro-2-hydroxy-N-(4-methyl-3,5-bis(trifluoromethyl)phenyl)benzamide

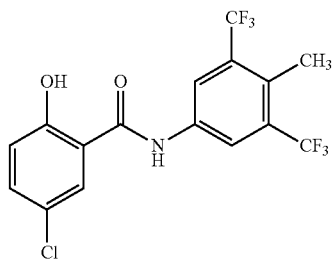 [SMILES: Cc1c(C(F)(F)F)cc(NC(=O)c2cc(Cl)ccc2O)cc1C(F)(F)F]

1010 mg of the target compound (yield: 51%) was obtained by the same manner as described in Example 1 except that 4-methyl-3,5-bis(trifluoromethyl)aniline was used instead of 3,5-bis(trifluoromethyl)aniline.

m.p: 192-193° C.;

¹H-NMR (300 MHz, DMSO-d⁶) δ 2.49 (s, 3H), 7.02 (d, J=8.8 Hz, 1H), 7.47 (dd, J=8.8, 2.7 Hz, 1H), 7.87 (d, J=2.6, 1H), 8.41 (s, 2H), 10.75 (s, 1H), 11.48 (s, 1H).

EXAMPLE 34

Preparation of N-(3,5-bis(trifluoromethyl)phenyl)-5-chloro-2-hydroxy-3-methylbenzamide

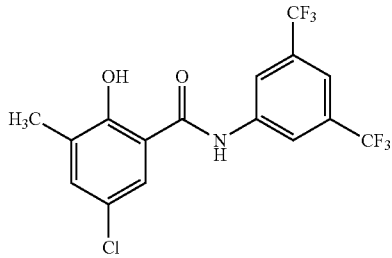 [SMILES: Cc1cc(Cl)cc(C(=O)Nc2cc(C(F)(F)F)cc(C(F)(F)F)c2)c1O]

Step 1: Preparation of N-(3,5-bis(trifluoromethyl)phenyl)-5-chloro-2-methoxy-3-methylbenzamide 1500 mg of the target compound (yield: 94%) was obtained by the same manner as described in Example 1 except that 5-chloro-2-methoxy-3-methylbenzoic acid was used instead of 5-chlorosalicylic acid.

$^1$H-NMR (300 MHz, DMSO-d$^6$) δ 2.29 (s, 3H), 3.75 (s, 3H), 7.49-7.51 (m, 2H), 7.83 (s, 1H), 8.41 (s, 2H), 11.00 (s, 1H).

Step 2: Preparation of N-(3,5-bis(trifluoromethyl)phenyl)-5-chloro-2-hydroxy-3-methylbenzamide N-(3,5-bis(trifluoromethyl)phenyl)-5-chloro-2-methoxy-3-methylbenzamide (1 g, 2.43 mmol) prepared in step 1 was dissolved in CH$_2$Cl$_2$ (15 ml), to which boron tribromide (3.54 ml, 12.15 mmol) was added at −70° C., followed by stirring at room temperature for 3 hours. The mixture was dropped in 20 ml of cold ice water, followed by stirring for 30 more minutes. The mixture was cooled down at room temperature, to which aqueous sodium hydroxide was dropped 6~7 drops. Extraction was performed with dichloromethane. The organic extract was mixed, dried over MgSO$_4$, and concentrated under reduced pressure, followed by chromatography (ethylacetate:hexane=1:5) to give 930 mg of the target compound (yield: 96%).

$^1$H-NMR (300 MHz, DMSO-d$^6$) δ 2.20 (s, 3H), 7.49 (d, J=1.8 Hz, 1H), 7.89 (s, 1H), 7.98 (d, J=2.4 Hz, 1H), 8.43 (s, 2H), 10.91 (s, 1H), 11.86 (s, 1H).

EXAMPLE 35

Preparation of 5-acetamido-N-(3,5-bis(trifluoromethyl)phenyl)-2-hydroxybenzamide

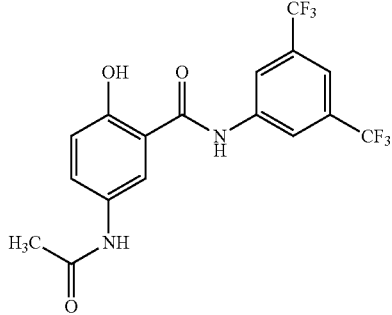 [SMILES: CC(=O)Nc1ccc(O)c(C(=O)Nc2cc(C(F)(F)F)cc(C(F)(F)F)c2)c1]

5-Amino-N-(3,5-bis(trifluoromethyl)phenyl)-2-hydroxybenzamide (364.24 mg, 1 mmol) obtained in Example 31 was dissolved in acetic anhydride (0.09 ., 1 mmol), to which AcOH (3 ml) was added, followed by stirring at room temperature for 3 hours. The mixture was extracted by using ethylacetate. The extract was washed with saturated sodium hydrogen carbonate, and dried over MgSO$_4$. After eliminating ethylacetate, the non-purified compound was purified by silica gel column chromatography (ethylacetate:hexane=1:1) to give 340 mg of the target compound (yield: 84%).

$^1$H-NMR (300 MHz, DMSO-d$^6$) δ 2.01 (s, 3H), 6.94 (d, J=8.8 Hz, 1H), 7.58 (dd, J=8.8, 2.6 Hz, 1H), 7.80 (s, 1H), 7.98 (d, J=2.6 Hz, 1H), 8.44 (s, 2H), 9.87 (s, 1H), 11.18 (s, 2H).

EXAMPLE 36

Preparation of 5-chloro-2-hydroxy-N-(2-nitro-4-trifluoromethyl-phenyl)-benzamide

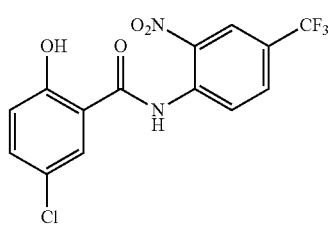 [SMILES: O=C(Nc1ccc(C(F)(F)F)cc1[N+](=O)[O-])c1cc(Cl)ccc1O]

166 mg of the target compound (yield: 9.2%) was obtained by the same manner as described in Example 1 except that 2-nitro-4-(trifluoromethyl)aniline was used instead of 3,5-bis(trifluoromethyl)aniline.

$^1$H-NMR (300 MHz, DMSO-d$^6$) δ 7.08 (dd, J=8.7, 1.2 Hz, 1H), 7.51-7.55 (m, 1H), 7.94 (dd, J=2.7, 1.4 Hz, 1H), 8.15-8.18 (m, 1H), 8.45 (s, 1H), 8.88 (d, J=9.0 Hz, 1H), 12.20 (s, 1H).

EXAMPLE 37

Preparation of 5-chloro-N-(5-cyano-pyridine-2-yl)-2-hydroxy-benzamide

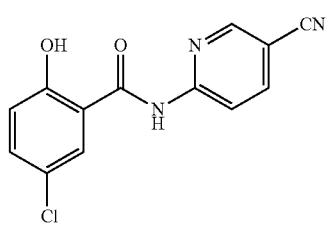

mg of the target compound (yield: 3%) was obtained by the same manner as described in Example 1 except that 6-aminonicotinonitrile was used instead of 3,5-bis(trifluoromethyl)aniline.

$^1$H-NMR (300 MHz, DMSO-d$^6$) δ 7.09 (d, J=8.8 Hz, 1H), 7.52 (dd, J=8.8, 2.8 Hz, 1H), 7.92 (d, J=2.8 Hz, 1H), 8.32-8.41 (m, 2H), 8.83 (t, J=1.3 Hz, 1H), 11.21 (s, 1H), 12.09 (s, 1H).

EXAMPLE 38

Preparation of N³-(3,5-bis-trifluoromethyl-phenyl)-4-hydroxy-isophthalamide

Step 1: Preparation of N-(3,5-bis-trifluoromethyl-phenyl)-5-cyano-2-hydroxy-benzamide

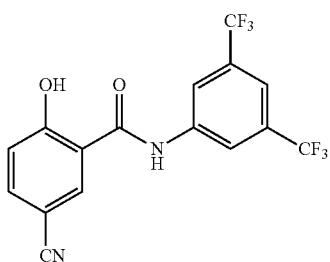 [SMILES: N#Cc1ccc(O)c(C(=O)Nc2cc(C(F)(F)F)cc(C(F)(F)F)c2)c1]

973 mg of the target compound (yield: 52%) was obtained by the same manner as described in Example 1 except that 5-cyano-2-hydroxybenzoic acid was used instead of 5-chlorosalicylic acid.

¹H-NMR (300 MHz, DMSO-d⁶) δ 7.15 (d, J=8.6 Hz, 1H), 7.85-7.89 (m, 2H), 8.22 (d, J=2.1 Hz, 1H), 8.44 (s, 2H), 10.98 (s, 1H), 12.10 (s, 1H).

Step 2: Preparation of N-(3,5-bis-trifluoromethyl-phenyl)-4-hydroxy-isophthalamide

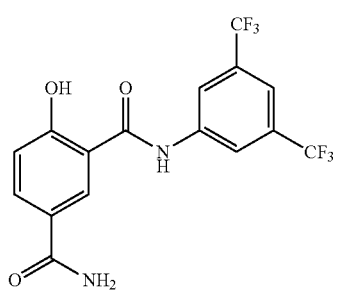 [SMILES: NC(=O)c1ccc(O)c(C(=O)Nc2cc(C(F)(F)F)cc(C(F)(F)F)c2)c1]

N-(3,5-bis-trifluoromethyl-phenyl)-5-cyano-2-hydroxy-benzamide (150 mg, 0.4 mmol) obtained in step 1 was dissolved in ethanol (1.74 ml) and DMSO (0.8 ml). 1 M NaOH (0.33 ml) was added thereto, to which 30% H₂O₂ (0.33 ml) was added. The reaction mixture was stirred overnight at room temperature. The solution was eliminated under reduced pressure. The residue proceeded to column chromatography (5% MeOH—CHCl₃) to give 149 mg of the target compound (yield: 95%).

m.p: 227-228° C.;

¹H-NMR (300 MHz, DMSO-d⁶) δ 7.05 (d, J=8.6 Hz, 1H), 7.30-7.32 (m, 1H), 7.86 (s, 1H), 7.92-7.94 (m, 1H), 7.97 (dd, J=8.7, 2.1 Hz, 1H), 8.42 (d, J=2.1 Hz, 1H), 8.49 (s, 2H), 10.98 (s, 1H), 11.65 (s, 1H).

EXAMPLE 39

Preparation of 5-chloro-2-hydroxy-N-(4-methoxy-3,5-bis-trifluoromethyl-phenyl)-benzamide

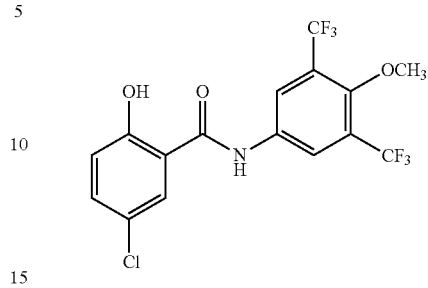

889 mg of the target compound (yield: 43%) was obtained by the same manner as described in Example 1 except that 3-methoxy-2,4-bis(trifluoromethyl)aniline was used instead of 3,5-bis(trifluoromethyl)aniline.

m.p: 168-170° C.;

¹H-NMR (300 MHz, CDCl₃) δ 3.97 (s, 3H), 7.02 (d, J=8.82 Hz, 1H), 7.42-7.51 (m, 2H), 7.97 (d, J=0.54 Hz, 1H), 8.08 (s, 2H), 11.39 (s, 1H).

EXAMPLE 40

Preparation of 5-chloro-2-hydroxy-N-(pyridine-2-yl)benzamide

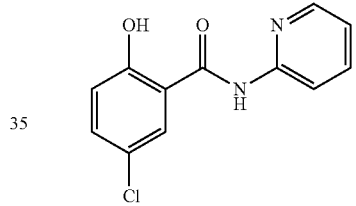

137 mg of the target compound (yield: 11%) was obtained by the same manner as described in Example 1 except that pyridine-2-amine was used instead of 3,5-bis(trifluoromethyl)aniline.

¹H-NMR (300 MHz, DMSO-d⁶) δ 7.06 (d, J=8.7 Hz, 1H), 7.17 (dd, J=6.8, 5.1 Hz, 1H), 7.49 (dd, J=8.7, 2.8 Hz, 1H), 7.83-7.88 (m, 1H), 7.96 (d, J=2.7 Hz, 1H), 8.24 (d, J=8.3 Hz, 1H), 8.35 (d, J=3.9 Hz, 1H), 10.95 (bs, 1H).

EXAMPLE 41

Preparation of 5-chloro-2-hydroxy-N-(5-(trifluoromethyl)pyridine-2-yl)benzamide

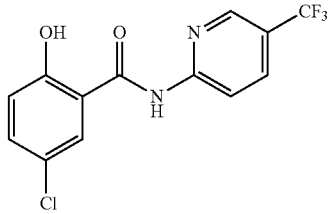 [SMILES: O=C(Nc1ccc(C(F)(F)F)cn1)c1cc(Cl)ccc1O]

341 mg of the target compound (yield: 26%) was obtained by the same manner as described in Example 1 except that 5-(trifluoromethyl)pyridine-2-amine was used instead of 3,5-bis(trifluoromethyl)aniline.

m.p: 241-243° C.;

¹H-NMR (300 MHz, DMSO-d⁶) δ 7.08 (d, J=8.7 Hz, 1H), 7.51 (dd, J=8.7, 2.8 Hz, 1H), 7.93 (d, J=2.7 Hz, 1H), 8.26 (dd, J=8.8, 2.2 Hz, 1H), 8.43 (d, J=8.7 Hz, 1H), 8.74 (d, J=1.4 Hz, 1H), 11.18 (bs, 1H).

EXAMPLE 42

Preparation of 5-chloro-N-(5-chloropyridine-2-yl)-2-hydroxybenzamide

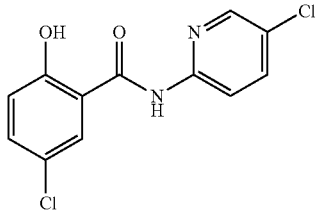 [SMILES: O=C(Nc1ccc(Cl)cn1)c1cc(Cl)ccc1O]

184 mg of the target compound (yield: 13%) was obtained by the same manner as described in Example 1 except that 5-(chloro)pyridine-2-amine was used instead of 3,5-bis(trifluoromethyl)aniline.

¹H-NMR (300 MHz, DMSO-d⁶) δ 7.07 (d, J=8.7 Hz, 1H), 7.49 (dd, J=8.7, 2.8 Hz, 1H), 7.94 (d, J=2.7 Hz, 1H), 7.98 (dd, J=8.9, 2.6 Hz, 1H), 8.27 (d, J=8.9 Hz, 1H), 8.41 (d, J=2.1 Hz, 1H), 10.99 (bs, 1H).

EXAMPLE 43

Preparation of 5-chloro-2-hydroxy-N-(perfluoropyridine-4-yl)benzamide

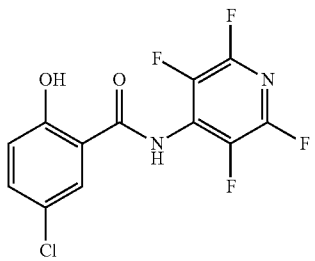 [SMILES: O=C(Nc1c(F)c(F)nc(F)c1F)c1cc(Cl)ccc1O]

112 mg of the target compound (yield: 7%) was obtained by the same manner as described in Example 1 except that 3-(cyano)benzamine was used instead of 3,5-bis(trifluoromethyl)aniline.

¹H-NMR (300 MHz, DMSO-d⁶) δ 7.07 (d, J=8.8 Hz, 1H), 7.53 (dd, J=8.8, 2.7 Hz, 1H), 7.86 (d, J=2.7 Hz, 1H).

EXAMPLE 44

Preparation of 5-chloro-N-(2-chloropyridine-3-yl)-2-hydroxybenzamide

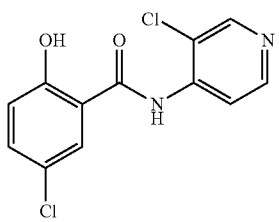 [SMILES: O=C(Nc1ccncc1Cl)c1cc(Cl)ccc1O]

297 mg of the target compound (yield: 21%) was obtained by the same manner as described in Example 1 except that 3-chloropyridine-4-amine was used instead of 3,5-bis(trifluoromethyl)aniline.

¹H-NMR (300 MHz, DMSO-d⁶) δ 7.08 (d, J=8.8 Hz, 1H), 7.48-7.54 (m, 2H), 7.96 (d, J=2.6 Hz, 2H), 8.19 (d, J=4.5 Hz, 1H), 8.79 (d, J=8.1 Hz, 1H), 11.02 (bs, 1H).

EXAMPLE 45

Preparation of 5-chloro-N-(6-chloropyridine-3-yl)-2-hydroxybenzamide

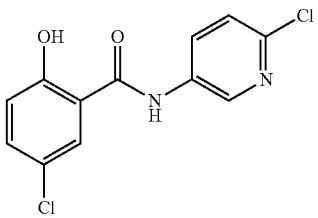 [SMILES: O=C(Nc1ccc(Cl)nc1)c1cc(Cl)ccc1O]

156 mg of the target compound (yield: 11%) was obtained by the same manner as described in Example 1 except that 6-chloropyridine-3-amine was used instead of 3,5-bis(trifluoromethyl)aniline.

m.p: 250-252° C.;

¹H-NMR (300 MHz, DMSO-d⁶) δ 7.01 (d, J=8.7 Hz, 1H), 7.46 (dd, J=8.7, 2.7 Hz, 1H), 7.53 (d, J=8.7 Hz, 1H), 8.20 (dd, J=8.6, 2.7 Hz, 1H), 8.72 (d, J=2.6 Hz, 1H), 10.79 (bs, 1H).

EXAMPLE 46

Preparation of 5-chloro-N-(3-chloro-5-(trifluoromethyl)pyridine-2-yl)-2-hydroxybenzamide

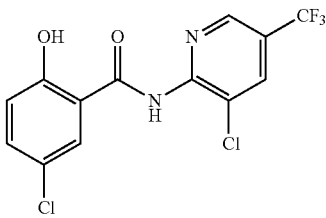 [SMILES: O=C(Nc1ncc(C(F)(F)F)cc1Cl)c1cc(Cl)ccc1O]

119 mg of the target compound (yield: 8%) was obtained by the same manner as described in Example 1 except that 3-chloro-5-(trifluoromethyl)pyridine-2-amine was used instead of 3,5-bis(trifluoromethyl)aniline.

¹H-NMR (300 MHz, DMSO-d⁶) δ 7.21 (d, J=8.7 Hz, 1H), 7.67 (dd, J=8.6, 2.5 Hz, 1H), 7.84 (d, J=2.5 Hz, 1H), 8.61 (s, 1H), 8.91 (s, 1H).

EXAMPLE 47

Preparation of 5-chloro-N-(2-chloropyridine-4-yl)-2-hydroxybenzamide

Step 1: Preparation of 4-chloro-2-(2-chloropyridine-4-ylcarbamoyl)phenylbenzonate

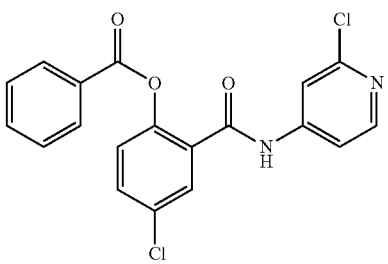 [SMILES: O=C(Oc1ccc(Cl)cc1C(=O)Nc1ccnc(Cl)c1)c1ccccc1]

4-Chloro-2-(chlorocarbonyl)phenylbenzonate (1.18 mg, 4 mmol) was dissolved in toluene (18 ml). Triethylamine (0.66 mL, 4.8 mmol) was added thereto, to which 4-amino-2-chloropyridine (460 mg, 3.6 mmol) was added, followed by reflux-stirring. Upon completion of the reaction, column chromatography (ethylacetate:hexane=1:5) was performed to give 540 mg of the target compound (yield: 23%).

$^1$H-NMR (300 MHz, CDCl$_3$) δ 7.22 (dd, J=5.6, 1.8 Hz, 1H), 7.26 (d, J=8.6 Hz, 1H), 7.48 (d, J=1.6 Hz, 1H), 7.54-7.59 (m, 3H), 7.72 (t, J=7.4 Hz, 1H), 7.92 (d, J=2.5 Hz, 1H), 8.16 (s, 1H), 8.19 (d, J=2.5 Hz, 1H), 8.59 (bs, 1H).

Step 2: Preparation of 5-chloro-N-(2-chloropyridine-4-yl)-2-hydroxybenzamide

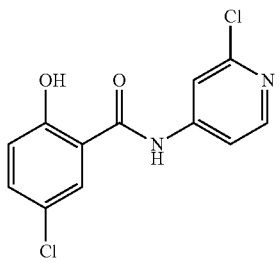 [SMILES: O=C(Nc1ccnc(Cl)c1)c1cc(Cl)ccc1O]

4-Chloro-2-(2-chloropyridine-4-ylcarbamoyl)phenylbenzonate (560 mg, 1.2 mmol) obtained in step 1 was added in the mixed solution of methanol (5 .) and 1,4-dioxane (5 mL), to which potassium carbonate (K$_2$CO$_3$, 244 mg, 1.8 mmol) was added. Upon completion of the reaction, column chromatography (ethylacetate:hexane=1:5) was performed to give 272 mg of the target compound (yield: 80%).

m.p: 223-225° C.;

$^1$H-NMR (300 MHz, DMSO-d$^6$) δ 7.03 (d, J=8.8 Hz, 1H), 7.47 (dd, J=8.7, 2.6 Hz, 1H), 7.66 (dd, J=5.6, 1.7 Hz, 1H), 7.77 (d, J=2.6 Hz, 1H), 7.90 (d, J=1.5 Hz, 1H), 8.31 (d, J=5.6 Hz, 1H), 10.78 (s, 1H), 11.36 (s, 1H).

EXAMPLE 48

Preparation of 5-chloro-N-(4,6-dimethylpyrimidine-2-yl)-2-hydroxybenzamide

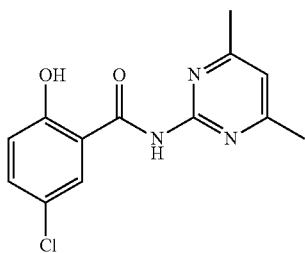 [SMILES: Cc1cc(C)nc(NC(=O)c2cc(Cl)ccc2O)n1]

mg of the target compound (yield: 14%) was obtained by the same manner as described in Example 1 except that 4,6-dimethylpyridine-2-amine was used instead of 3,5-bis(trifluoromethyl)aniline.

$^1$H-NMR (300 MHz, DMSO-d$^6$) δ 2.38 (s, 6H), 7.02 (t, J=4.3 Hz, 1H), 7.47 (dd, J=8.7, 2.6 Hz, 1H), 7.92 (d, J=2.6 Hz, 1H), 10.92 (s, 1H), 11.92 (s, 1H).

EXAMPLE 49

Preparation of 5-chloro-2-hydroxy-N-(pyrimidine-2-yl)benzamide

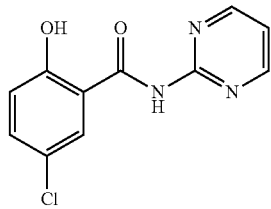 [SMILES: O=C(Nc1ncccn1)c1cc(Cl)ccc1O]

87 mg of the target compound (yield: 29%) was obtained by the same manner as described in Example 1 except that pyridine-2-amine was used instead of 3,5-bis(trifluoromethyl)aniline.

m.p: 248-251° C.;

$^1$H-NMR (300 MHz, DMSO-d$^6$) δ 7.03 (d, J=8.7 Hz, 1H), 7.26 (t, J=4.8 Hz, 1H), 7.41-7.51 (m, 2H), 7.90 (d, J=2.6 Hz, 1H), 8.71 (d, J=4.8 Hz, 2H), 11.15 (s, 1H).

EXAMPLE 50

Preparation of 5-chloro-2-hydroxy-N-(4-methylthiazole-2-yl)benzamide

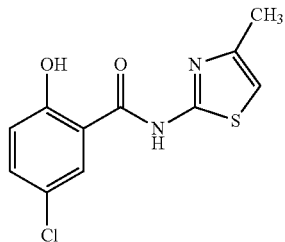 [SMILES: Cc1csc(NC(=O)c2cc(Cl)ccc2O)n1]

121 mg of the target compound (yield: 9%) was obtained by the same manner as described in Example 1 except that 4-methylthiazole-2-amine was used instead of 3,5-bis(trifluoromethyl)aniline.

$^1$H-NMR (300 MHz, DMSO-d$^6$) δ 2.27 (s, 3H), 6.79 (s, 1H), 6.96 (d, J=8.7 Hz, 1H), 7.43 (dd, J=8.8, 2.6 Hz, 1H), 7.89 (d, J=2.7 Hz, 1H).

EXAMPLE 51

Preparation of 5-chloro-2-hydroxy-N-(thiazole-2-yl)benzamide

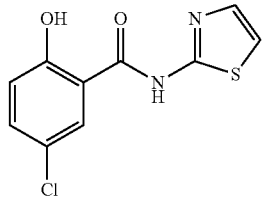 [SMILES: O=C(Nc1nccs1)c1cc(Cl)ccc1O]

140 mg of the target compound (yield: 11%) was obtained by the same manner as described in Example 1 except that thiazole-2-amine was used instead of 3,5-bis(trifluoromethyl)aniline.

$^1$H-NMR (300 MHz, DMSO-d$^6$) δ 6.99 (d, J=8.7 Hz, 1H), 7.26 (d, J=3.8 Hz, 1H), 7.46 (dd, J=8.7, 2.5 Hz, 1H), 7.57 (d, J=3.9 Hz, 1H), 7.91 (d, J=2.6 Hz, 1H).

EXAMPLE 52

Preparation of 5-chloro-2-hydroxy-N-(4-(trifluoromethyl)thiazole-2-yl)benzamide

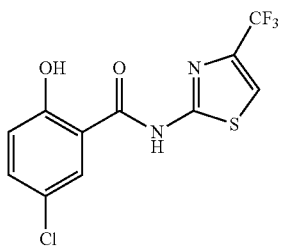 [SMILES: O=C(Nc1nc(C(F)(F)F)cs1)c1cc(Cl)ccc1O]

436 mg of the target compound (yield: 27%) was obtained by the same manner as described in Example 1 except that 4-(trifluoromethyl)-2-amine was used instead of 3,5-bis(trifluoromethyl)aniline.

$^1$H-NMR (300 MHz, DMSO-d$^6$) δ 7.07 (d, J=8.8 Hz, 1H), 7.52 (dd, J=8.8, 2.6 Hz, 1H), 7.89 (d, J=2.6 Hz, 1H), 8.05 (s, 1H), 11.69 (s, 1H), 12.33 (s, 1H).

EXAMPLE 53

Preparation of 5-chloro-2-hydroxy-N-(4-phenylthiazole-2-yl)benzamide

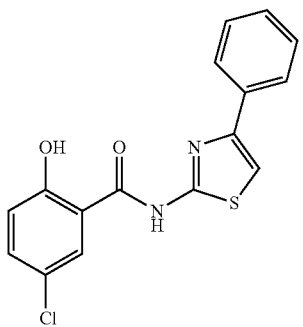 [SMILES: O=C(Nc1nc(-c2ccccc2)cs1)c1cc(Cl)ccc1O]

103 mg of the target compound (yield: 26%) was obtained by the same manner as described in Example 1 except that 4-phenylthiazole-2-amine was used instead of 3,5-bis(trifluoromethyl)aniline.

$^1$H-NMR (300 MHz, DMSO-d$^6$) δ 7.04 (d, J=8.8 Hz, 1H), 7.31 (t, J=7.1 Hz, 1H), 7.41 (t, J=7.4 Hz, 2H), 7.48 (dd, J=8.7, 2.4 Hz, 1H), 7.68 (s, 1H), 7.89 (d, J=7.5 Hz, 1H), 7.93 (d, J=2.7 Hz, 1H), 12.12 (s, 1H).

EXAMPLE 54

Preparation of N-(3,5-bis(trifluoromethyl)phenyl)-4-chloro-2-hydroxybenzamide

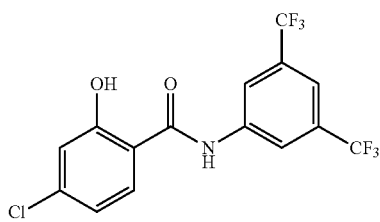 [SMILES: O=C(Nc1cc(C(F)(F)F)cc(C(F)(F)F)c1)c1ccc(Cl)cc1O]

The target compound (yield: 52%) was obtained by the same manner as described in Example 1 except that 4-chloro-2-hydroxybenzoic acid was used instead of 5-chlorosalicylic acid.

mp. 204-205° C.;

$^1$H-NMR (300 MHz, DMSO-d$^6$) δ 11.52 (brs, 1H), 10.80 (s, 1H), 8.43 (s, 2H), 7.81-7.86 (m, 2H), 7.03-7.06 (m, 2H).

EXAMPLE 55

Preparation of N-(3,5-bis(trifluoromethyl)phenyl)-2-hydroxy-5-nitrobenzamide

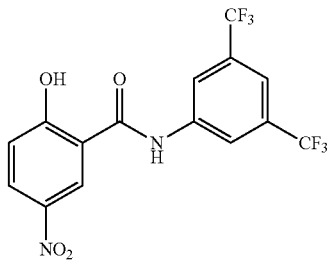 [SMILES: O=C(Nc1cc(C(F)(F)F)cc(C(F)(F)F)c1)c1cc([N+](=O)[O-])ccc1O]

The target compound (yield: 26%) was obtained by the same manner as described in Example 1 except that 2-hydroxy-5-nitrobenzoic acid was used instead of 5-chlorosalicylic acid.

mp. 225-226° C.;

$^1$H-NMR (300 MHz, DMSO-d$^6$) δ 11.13 (s, 1H), 8.69 (s, 1H), 8.45 (s, 2H), 8.30 (d, J=9.1 Hz, 1H), 7.87 (s, 1H), 7.17 (d, J=8.9 Hz, 1H).

EXAMPLE 56

Preparation of N-(3,5-bis(trifluoromethyl)phenyl)-5-cyano-2-hydroxybenzamide

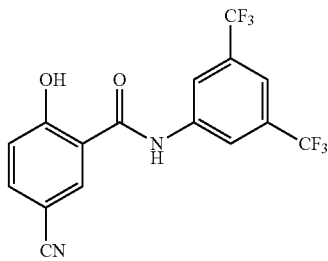 [SMILES: N#Cc1ccc(O)c(C(=O)Nc2cc(C(F)(F)F)cc(C(F)(F)F)c2)c1]

The target compound (yield: 52%) was obtained by the same manner as described in Example 1 except that 5-cyano-2-hydroxybenzoic acid was used instead of 5-chlorosalicylic acid.

mp. 251-253° C.;

$^1$H-NMR (300 MHz, DMSO-d$^6$) δ 12.10 (brs, 1H), 10.98 (s, 1H), 8.44 (s, 2H), 8.22 (d, J=2.1 Hz, 1H), 7.85-7.89 (m, 2H), 7.15 (d, J=8.6 Hz, 1H).

EXAMPLE 57

Preparation of 2-(3,5-bis(trifluoromethyl)phenylcarbamoyl)-4-chlorophenylacetate

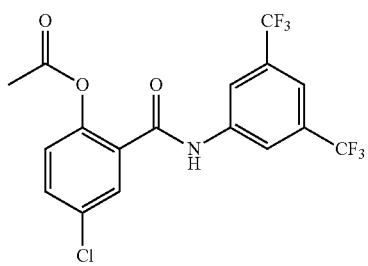 [SMILES: CC(=O)Oc1ccc(Cl)cc1C(=O)Nc1cc(C(F)(F)F)cc(C(F)(F)F)c1]

Step 1: Preparation of N-(3,5-bis(trifluoromethyl)phenyl)-5-chloro-2-hydroxybenzamide The target compound was obtained by the same manner as described in Example 1.
*¹H-NMR (300 MHz, DMSO-d⁶): δ 7.05 (1H, d, J=8.7 Hz), 7.49 (1H, dd, J=8.7, 2.7 Hz), 7.85 (1H, s), 7.87 (1H, d, J=2.7 Hz), 8.45 (2H, s), 10.85 (1H, s), 11.39 (1H, s).

Step 2: Preparation of 2-(3,5-bis(trifluoromethyl)phenylcarbamoyl)-4-chlorophenylacetate N-(3,5-bis(trifluoromethyl)phenyl)-5-chloro-2-hydroxybenzamide (191.8 mg) obtained in step 1 was dissolved in dimethylformamide (DMF, 1.5 ml), to which acetic anhydride (0.99 ., 10.5 mmol) was added. The reaction mixture was stirred at 100° C. for 4 hours, which was filtered and washed with n-hexane. The washed reactant was dried to give 115.6 mg of the target compound (yield: 54%).
mp. 117-118° C.;
¹H-NMR (300 MHz, DMSO-d⁶) δ 11.06 (s, 1H), 8.37 (s, 2H), 7.86-7.90 (m, 2H), 7.71 (dd, J=8.7 Hz, J=2.6 Hz, 1H), 7.36 (d, J=8.7 Hz, 1H), 2.23 (s, 3H).

EXAMPLE 58

Preparation of 2-benzyloxy-N-(3,5-bis-trifluoromethyl-phenyl)-5-chlorobenzamide

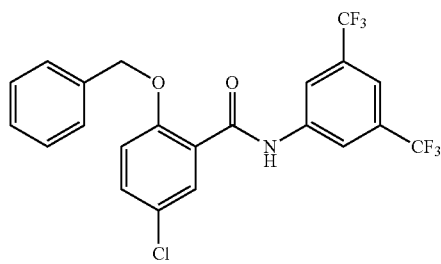 [SMILES: O=C(Nc1cc(C(F)(F)F)cc(C(F)(F)F)c1)c1cc(Cl)ccc1OCc1ccccc1]

Step 1: Preparation of N-(3,5-bis(trifluoromethyl)phenyl)-5-chloro-2-hydroxybenzamide The target compound was obtained by the same manner as described in Example 1.
¹H-NMR (300 MHz, DMSO-d⁶): δ 7.05 (1H, d, J=8.7 Hz), 7.49 (1H, dd, J=8.7, 2.7 Hz), 7.85 (1H, s), 7.87 (1H, d, J=2.7 Hz), 8.45 (2H, s), 10.85 (1H, s), 11.39 (1H, s).

Step 2: Preparation of 2-benzyloxy-N-(3,5-bis-trifluoromethyl-phenyl)-5-chlorobenzamide N-(3,5-bis(trifluoromethyl)phenyl)-5-chloro-2-hydroxybenzamide (191.8 mg) obtained in step 1 was dissolved in dimethylformamide (DMF, 1.5 ml), to which benzylbromide (0.07 ., 0.55 mmol) and potassium carbonate (K₂CO₃, 82.9 mg, 0.6 mmol) were added. The reaction mixture was stirred at room temperature for 4 hours. Dimethylformamide was distillated under reduced pressure, followed by extraction with ethylacetate (EtOAc). The extracted organic layer was dried over MgSO₄, filtered and concentrated. The concentrated reactant was separated by column chromatography (developing solvent: hexane/ethylacetate=15/1) to give 220 mg of the target compound (yield: 93%).
mp. 178-180° C.;
¹H-NMR (300 MHz, DMSO-d⁶) δ 10.84 (s, 1H), 8.26 (s, 1H), 7.80 (s, 1H), 7.68 (d, J=2.73 Hz, 1H), 7.60 (dd, J=11.6 Hz, J=2.7 Hz, 1H), 7.47-7.48 (m, 2H), 7.30-7.34 (m, 4H), 5.23 (s, 2H).

EXAMPLE 59

Preparation of 5-chloro-2-hydroxy-N-phenylbenzamide

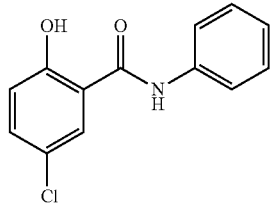 [SMILES: O=C(Nc1ccccc1)c1cc(Cl)ccc1O]

The target compound (yield: 16%) was obtained by the same manner as described in Example 1 except that aniline was used instead of 3,5-bis(trifluoromethyl)aniline.
mp. 211-212° C.;
¹H-NMR (300 MHz, DMSO-d⁶) δ 11.84 (s, 1H), 10.40 (s, 1H), 7.96 (d, J=2.6 Hz, 1H), 7.69 (d, J=8.3 Hz, 2H), 7.46 (dd, J=8.8 Hz, J=2.7 Hz, 1H), 7.34-7.39 (m, 2H), 7.15 (dd, J=7.2 Hz, J=7.2 Hz, 1H), 7.00 (d, J=8.8 Hz, 1H).

EXAMPLE 60

Preparation of 5-chloro-N-(3,5-dimethylphenyl)-2-hydroxybenzamide

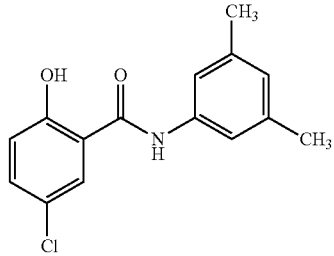 [SMILES: Cc1cc(C)cc(NC(=O)c2cc(Cl)ccc2O)c1]

The target compound (yield: 22%) was obtained by the same manner as described in Example 1 except that 3,5-dimethylaniline was used instead of 3,5-bis(trifluoromethyl)aniline.
mp. 183-184° C.;
¹H-NMR (300 MHz, DMSO-d⁶) δ 11.91 (s, 1H), 10.28 (s, 1H), 7.97 (d, J=2.6, 1H) 7.46 (dd, J=8.8 Hz, J=2.6 Hz, 1H), 7.32 (s, 2H), 7.00 (d, J=8.8 Hz, 1H), 6.79 (s, 1H), 2.49 (s, 6H).

EXAMPLE 61

Preparation of 5-chloro-N-(3,5-dichlorophenyl)-2-hydroxybenzamide

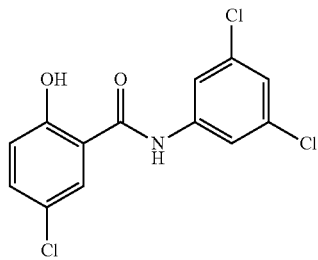 [SMILES: O=C(Nc1cc(Cl)cc(Cl)c1)c1cc(Cl)ccc1O]

The target compound (yield: 24%) was obtained by the same manner as described in Example 1 except that 3,5-dichloroaniline was used instead of 3,5-bis(trifluoromethyl)aniline.

mp. 247-249° C.;

$^1$H-NMR (300 MHz, DMSO-d$^6$) δ 11.44 (brs, 1H), 10.61 (s, 1H), 7.81-7.83 (m, 3H), 7.47 (dd, J=8.8 Hz, J=2.6 Hz, 1H), 7.36-7.37 (m, 1H), 7.02 (d, J=8.8 Hz, 1H).

EXAMPLE 62

Preparation of N-(3,4-bis(trifluoromethyl)phenyl)-5-chloro-2-hydroxybenzamide

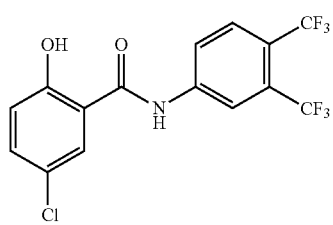

The target compound (yield: 5%) was obtained by the same manner as described in Example 1 except that 3,4-bis(trifluoromethyl)aniline was used instead of 3,5-bis(trifluoromethyl)aniline.

mp. 215-217° C.;

$^1$H-NMR (300 MHz, CDCl$_3$) δ 8.14-8.16 (m, 2H), 7.97 (d, J=2.3 Hz, 1H), 7.84 (d, J=8.6 Hz, 1H), 7.38 (dd, J=8.8 Hz, J=2.3 Hz, 1H), 6.95 (d, J=8.8 Hz, 1H).

EXAMPLE 63

Preparation of N-(4-bromo-3-(trifluoromethyl)phenyl)-5-chloro-2-hydroxybenzamide

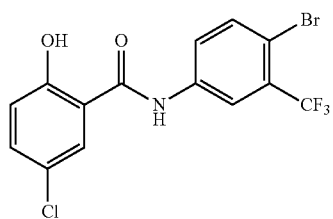

The target compound (yield: 26%) was obtained by the same manner as described in Example 1 except that 4-bromo-3-trifluoromethylaniline was used instead of 3,5-bis(trifluoromethyl)aniline.

mp. 238-240° C.;

$^1$H-NMR (300 MHz, DMSO-d$^6$) δ 11.53 (brs, 1H), 10.65 (s, 1H), 8.29 (s, 1H), 7.85-7.93 (m, 3H), 7.44-7.48 (dd, J=8.8 Hz, J=2.6 Hz, 1H), 7.02 (d, J=8.8 Hz, 1H).

EXAMPLE 64

Preparation of 5-chloro-N-(2-fluoro-5-(trifluoromethyl)phenyl)-2-hydroxybenzamide

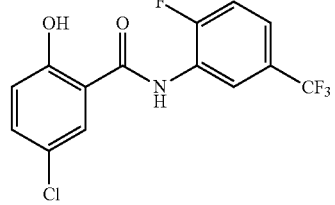

The target compound (yield: 38%) was obtained by the same manner as described in Example 1 except that 2-fluoro-5-trifluoromethylaniline was used instead of 3,5-bis(trifluoromethyl)aniline.

mp. 199-200;

$^1$H-NMR (300 MHz, DMSO-d$^6$) δ 12.25 (brs, 1H), 10.91 (s, 1H), 8.72 (d, J=8.2 Hz, 1H), 7.94 (d, J=2.8 Hz, 1H), 7.59 (d, J=8.1 Hz, 2H), 7.51 (dd, J=9.3 Hz, J=2.8 Hz, 1H), 7.06 (d, J=8.8 Hz, 1H).

EXAMPLE 65

Preparation of N-(4-bromo-3,5-bis(trifluoromethyl)phenyl)-5-chloro-2-hydroxybenzamide

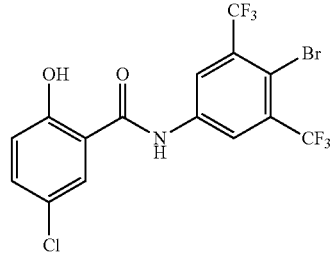 [SMILES: O=C(Nc1cc(C(F)(F)F)c(Br)c(C(F)(F)F)c1)c1cc(Cl)ccc1O]

The target compound (yield: 20%) was obtained by the same manner as described in Example 1 except that 4-bromo-3,5-bis(trifluoromethyl)aniline was used instead of 3,5-bis(trifluoromethyl)aniline.

mp. 196-197;

$^1$H-NMR (300 MHz, DMSO-d$^6$) δ 10.91 (s, 1H), 8.55 (s, 2H), 7.83 (d, J=2.7, 1H), 7.49 (dd, J=8.7 Hz J=2.7 Hz, 1H), 7.03 (d, J=8.7 Hz, 1H).

EXAMPLE 66

Preparation of 5-chloro-2-hydroxy-N-(3,4,5-trichloro-phenyl)benzamide

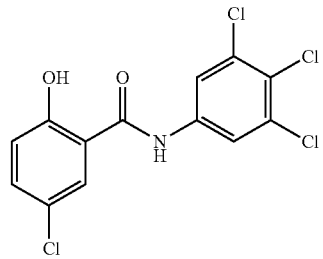 [SMILES: O=C(Nc1cc(Cl)c(Cl)c(Cl)c1)c1cc(Cl)ccc1O]

The target compound (yield: 44%) was obtained by the same manner as described in Example 1 except that 3,4,5-trichloroaniline was used instead of 3,5-bis(trifluoromethyl)aniline.

mp. 287-290;

$^1$H-NMR (300 MHz, DMSO-d$^6$) δ 11.41 (brs, 1H), 10.68 (s, 1H), 8.05 (s, 2H), 7.81 (d, J=2.5 Hz, 1H), 7.47 (dd, J=8.7 Hz, J=2.5 Hz, 1H), 7.02 (d, J=8.8 Hz, 1H).

EXAMPLE 67

Preparation of N-(3,5-bis(trifluoromethyl)phenyl)-5-chloro-2-hydroxynicotineamide

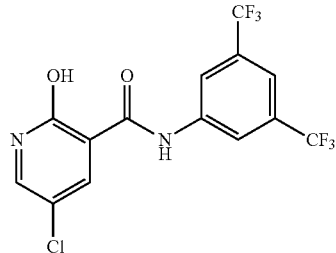 [SMILES: O=C(Nc1cc(C(F)(F)F)cc(C(F)(F)F)c1)c1cc(Cl)cnc1O]

The target compound (yield: 49%) was obtained by the same manner as described in Example 1 except that 5-chloro-2-hydroxynicotinic acid was used instead of 5-chlorosalicylic acid.

mp. 333-335;

$^1$H-NMR (300 MHz, DMSO-d$^6$) δ 13.29 (brs, 1H), 12.46 (s, 1H), 8.37 (s, 2H), 8.34 (d, J=2.7 Hz, 1H), 8.13 (d, J=2.9 Hz, 1H), 7.79 (s, 1H).

EXAMPLE 68

Preparation of N-(3,5-bis(trifluoromethyl)phenyl)-4-hydroxyquinoline-3-carboxamide

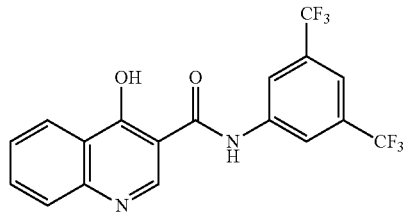 [SMILES: O=C(Nc1cc(C(F)(F)F)cc(C(F)(F)F)c1)c1cnc2ccccc2c1O]

The target compound (yield: 10%) was obtained by the same manner as described in Example 1 except that 4-hydroxyquinoline-3-carboxylic acid was used instead of 5-chlorosalicylic acid.

$^1$H-NMR (300 MHz, DMSO-d$^6$) δ 11.47 (s, 1H), 9.11 (s, 1H), 8.40 (s, 2H), 8.37 (d, J=8.3 Hz, 1H), 8.20 (d, J=8.2 Hz, 1H), 8.00 (dd, J=7.2 Hz, J=7.2 Hz, 1H), 7.87-7.91 (m, 2H).

EXAMPLE 69

Preparation of 5-chloro-N-(4,5-dihydrothiazol-2-yl)-2-hydroxybenzamide

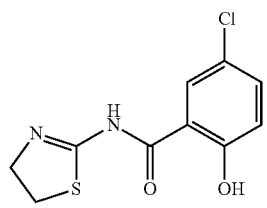 [SMILES: O=C(NC1=NCCS1)c1cc(Cl)ccc1O]

The target compound was purchased by Enamine (Enamine, Z68175643)

EXAMPLE 70

Preparation of 5-chloro-2-hydroxy-N-(4,5,6,7-tetrahydrobenzo[d]thiazol-2-yl)benzamide

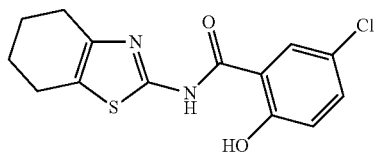 [SMILES: O=C(Nc1nc2c(s1)CCCC2)c1cc(Cl)ccc1O]

The target compound was purchased by Enamine (Enamine, Z68484867)

EXAMPLE 71

Preparation of 5-chloro-2-hydroxy-N-(5-methylthiazole-2-yl)benzamide

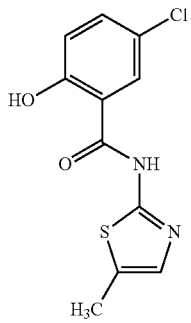 [SMILES: Cc1cnc(NC(=O)c2cc(Cl)ccc2O)s1]

The target compound was purchased by Enamine (Enamine, Z68683800)

EXAMPLE 72

Preparation of 5-chloro-N-(4,5-dimethylthiazol-2-yl)-2-hydroxybenzamide

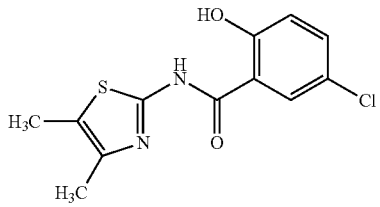 [SMILES: Cc1nc(NC(=O)c2cc(Cl)ccc2O)sc1C]

The target compound was purchased by Enamine (Enamine, Z203227614)

EXAMPLE 73

Preparation of 5-chloro-N-(4-((2,6-dimethylmorpholino)methyl)thiazol-2-yl)-2-hydroxybenzamide

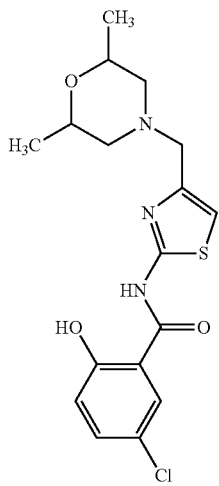 [SMILES: CC1CN(Cc2csc(NC(=O)c3cc(Cl)ccc3O)n2)CC(C)O1]

The target compound was purchased by Enamine (Enamine, Z230310192)

EXAMPLE 74

Preparation of 5-chloro-2-hydroxy-N-(1-methyl-1H-pyrazol-3-yl)benzamide

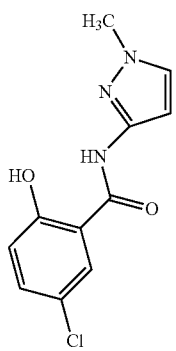 [SMILES: Cn1ccc(NC(=O)c2cc(Cl)ccc2O)n1]

The target compound was purchased by Enamine (Enamine, Z240293532)

EXAMPLE 75

Preparation of 5-chloro-2-hydroxy-N-(5-methyl-1H-1,2,4-triazol-3-yl)benzamide

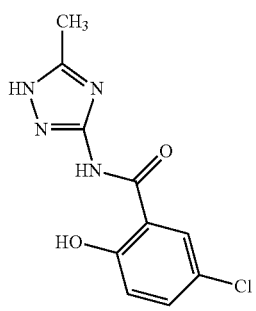 [SMILES: Cc1nc(NC(=O)c2cc(Cl)ccc2O)n[nH]1]

The target compound was purchased by Enamine (Enamine, Z1255527342)

EXAMPLE 76

Preparation of 5-chloro-2-hydroxy-N-(4-(pyridin-3-yl)thiazol-2-yl)benzamide

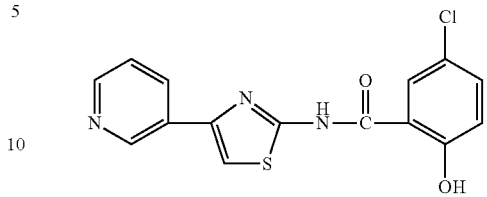

The target compound was purchased by Enamine (Enamine, Z68700988)

Experimental Example 1

Inhibitory Effect on TMPRSS4 Serine Protease Activity

The following experiment was performed to investigate the inhibitory effect of the compound of the present invention on the activity of TMPRSS4 serine protease expressed in cancer cells.

Step 1: Expression and Purification of TMPRSS4/MT-SP2 Serine Protease Domain

TMPRSS4 serine protease domain ($205^{th}$ Val~$437^{th}$ Leu) was cloned in pET21b/NdeI-XhoI, which was introduced in E. coli BL21 (DE3). At this time, FlagX2-enterokinase cleavage site (DYKDDDGDYKDDDDK; total 15 amino acids) was inserted in N-terminal of TMPRSS4 serine protease domain as shown in FIG. 1. The forward and reverse primers for PCR used for the cloning were presented by SEQ. ID. NO: 1 and NO: 2.

Figure 2:
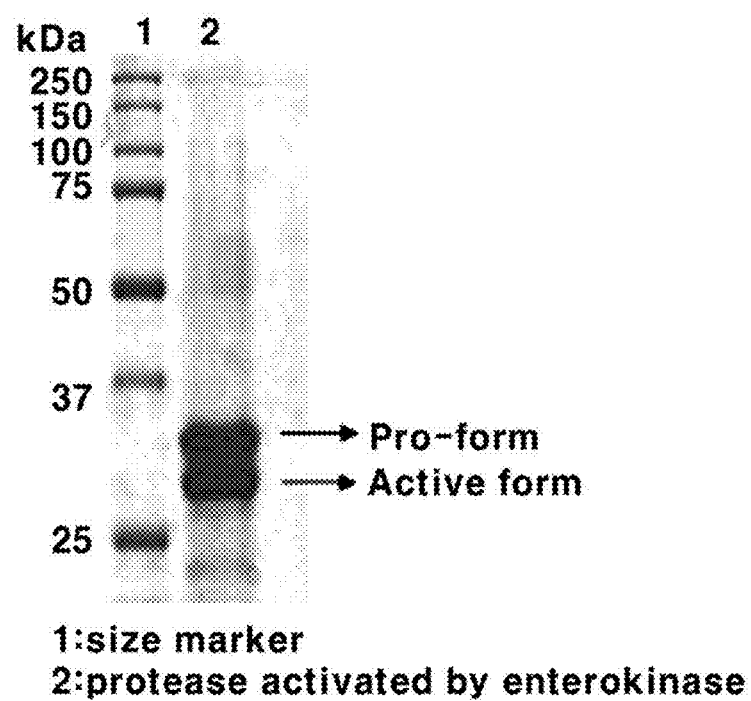
FIG. 2 is a diagram illustrating the effect of the treatment of enterokinase after the expression/purification of protein from E. coli of Experimental Example 1.

The cells were cultured in 10 ml of LB containing ampicillin at 37° C. overnight. IL of LB+ampicillin was added thereto, followed by further culture until OD reached 0.6~0.8. 0.1 mM IPTG was added thereto, followed by further culture for 16 hours. Cell pellet was obtained, purified by Ni-NTA (Qiagen), and dialyzed. TMPRSS4 serine protease (pro-form) labeled with 2 mg of 2Xflag-enterokinase cleavage site was conjugated to Ni-NTA resin (4°, overnight). Enterokinase (NEB) was treated thereto at the concentration of 0.0002%/w/w at room temperature for 5 hours. The sample was washed, eluted with 50 mM imidazole in 20 mM of sodium phosphate buffer, and then dialyzed. As a result, active form of TMPRSS4 serine protease was obtained (FIG. 2).

Figure 3:
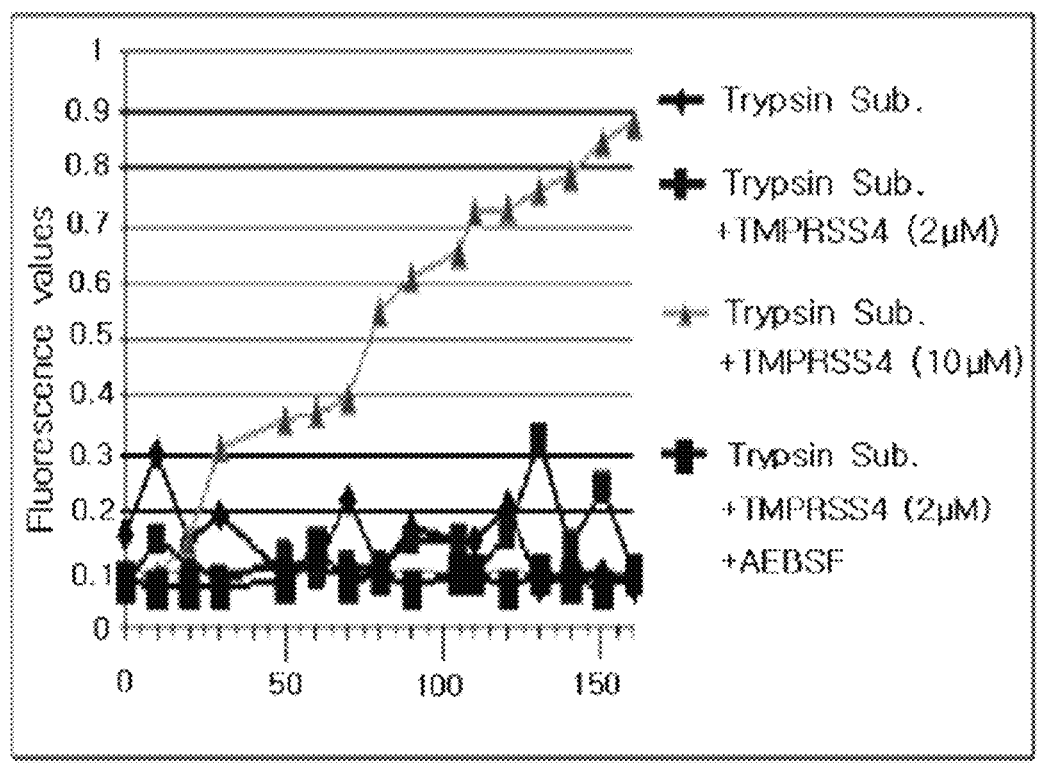
FIG. 3 is a diagram illustrating the activity against trypsin peptide matrix of Experimental Example 1.
Figure 4:
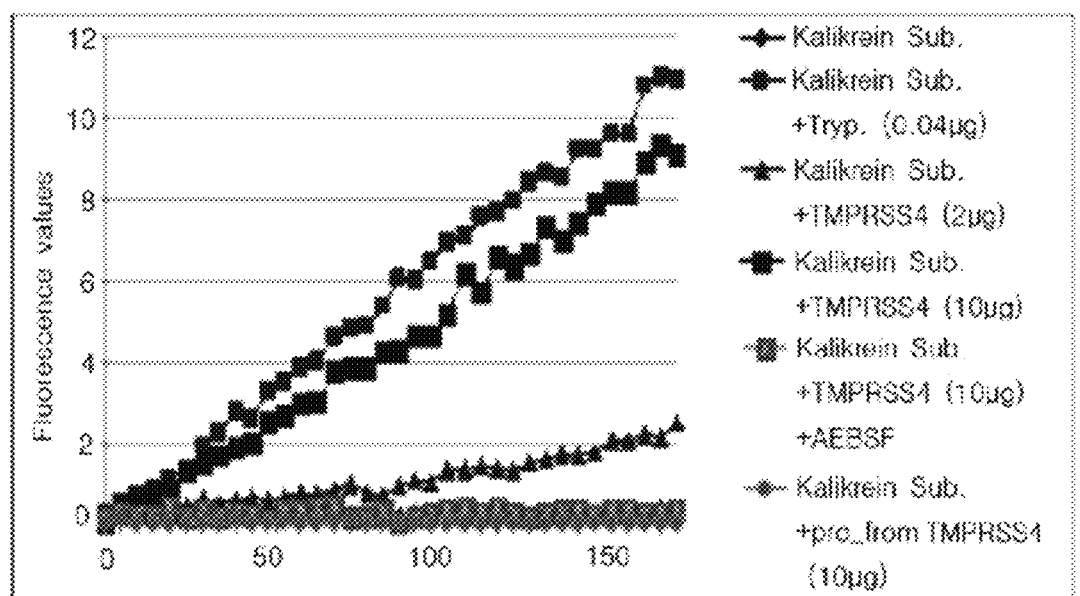
FIG. 4 is a diagram illustrating the activity against kallikrein peptide matrix of Experimental Example 1.

Step 2: Investigation of TMPRSS4 Serine Protease Activity Using Peptide Substrate To investigate whether or not the purified TMPRSS4 serine protease active form had protease activity, the following experiment was performed using trypsin peptide substrate (Boc-Gln-Ala-Arg-7-amido-4-methylcoumarin hydrochloride; Sigma B4153) and kallikrein peptide substrate (Z-Phe-Arg 7-amido-4-methylcoumarin hydrochloride; Sigma C9521). The protein activity was evaluated by measuring fluorescence shown during hydrolysis of the peptide. As a result, the TMPRSS4 serine protease active form could hydrolyze the peptide substrate dose-dependently. It was also confirmed that such activity was inhibited by 1 mM of AEBSF (Sigma), the conventional serine protease inhibitor. TMPRSS4 pro-form (before digesting with enterokinase) did not show any activity, as expected, and trypsin (Try (0.04 μg)) was used as the control (FIG. 3 and FIG. 4). Reaction was induced after adding 100 μM of the peptide substrate into reaction buffer (50 mM Tris-HCl (pH 8.0), 10 mM CaCl$_2$, 1 µM ZnCl$_2$). Then, fluorescence was measured at 5 minutes interval (excitation 385 nm, emission 455 nm).

The TMPRSS4 hydrolase activity of the compounds of Examples 1~68 was measured by the similar method to the above in order to evaluate the effect of the compounds: 2 µg of the TMPRSS4 serine protease active form and 100 µM kallikrein peptide substrate (Z-Phe-Arg7-amido-4-methylcoumarin hydrochloride; Sigma C9521) were mixed in reaction buffer (50 mM Tris-HCl (pH8.0), 10 mM CaCl$_2$, 1 µM ZnCl$_2$). Then, fluorescence (excitation 385 nm/emission 455 nm) was measured at 5 minutes interval for 150 minutes. At this time, after adding each compound of the present invention to the reaction buffer, reaction was induced and then the inhibitory effect of each compound on the TMPRSS4 serine protease activity was investigated. Dimethylsulfoxide (DMSO) was used as the negative control. The results are shown in Table 2.

TABLE 2

| Formula | Intracellular protease activity Inhibition % | | |
|---|---|---|---|
| | 100 uM | 30 uM | 10 uM |
| Example 1 | 100 | 96 | 64 |
| Example 2 | N/D | 100 | 100 |
| Example 3 | N/D | 64 | 0 |
| Example 4 | 98 | 86 | 64 |
| Example 5 | N/D | 20 | 0 |
| Example 6 | 99 | 88 | 67 |
| Example 7 | N/D | 53 | 0 |
| Example 8 | N/D | 96 | 58 |
| Example 9 | N/D | 84 | 54 |
| Example 10 | N/D | 91 | 37 |
| Example 11 | 88 | 47 | 12 |
| Example 12 | 69 | 29 | N/D |
| Example 13 | N/D | 79 | 32 |
| Example 14 | N/D | 55 | 0 |
| Example 15 | N/D | 100 | 22 |
| Example 16 | 98 | 93 | 80 |
| Example 17 | N/D | 77 | 29 |
| Example 18 | N/D | 54 | 46 |
| Example 19 | 100 | 88 | N/D |
| Example 20 | N/D | 100 | 40 |
| Example 21 | N/D | 100 | 100 |
| Example 22 | 100 | 100 | 64 |
| Example 23 | 100 | 99 | 64 |
| Example 24 | N/D | 63 | 36 |
| Example 25 | 75 | 8 | N/D |
| Example 26 | N/D | 93 | 61 |
| Example 27 | 100 | 92 | N/D |
| Example 28 | 100 | 75 | N/D |
| Example 29 | N/D | 100 | 43 |
| Example 30 | N/D | 31 | 5 |
| Example 31 | N/D | 30 | 3 |
| Example 32 | 99 | 95 | 71 |
| Example 33 | N/D | 94 | 51 |
| Example 34 | N/D | 78 | 33 |
| Example 35 | N/D | 0 | 0 |
| Example 36 | N/D | 98 | 53 |
| Example 37 | N/D | 63 | 26 |
| Example 38 | N/D | 21 | 0 |
| Example 39 | N/D | 80 | 56 |
| Example 40 | 11 | 0 | N/D |
| Example 41 | 47 | 25 | N/D |
| Example 42 | 55 | 14 | N/D |
| Example 43 | 51 | 31 | N/D |
| Example 44 | 18 | 8 | N/D |
| Example 45 | 39 | 6 | N/D |
| Example 46 | 0 | 0 | N/D |
| Example 47 | 21 | 35 | N/D |
| Example 48 | 0 | 0 | N/D |
| Example 49 | 2 | 0 | N/D |
| Example 50 | 67 | 0 | N/D |
| Example 51 | 90 | 44 | N/D |
| Example 52 | 100 | 61 | N/D |
| Example 53 | 98 | 91 | N/D |
| Example 54 | N/D | 74 | 29 |
| Example 55 | N/D | 78 | 33 |
| Example 56 | N/D | 53 | 15 |
| Example 57 | N/D | 4 | 0 |
| Example 58 | N/D | 6 | 0 |
| Example 59 | 75 | 13 | N/D |
| Example 60 | 56 | 44 | N/D |
| Example 61 | N/D | 58 | 15 |
| Example 62 | N/D | 59 | 37 |
| Example 63 | 98 | 46 | 30 |
| Example 64 | 100 | 100 | 67 |
| Example 65 | N/D | 85 | 58 |
| Example 66 | N/D | 23 | 6 |
| Example 67 | N/D | 19 | 0 |
| Example 68 | N/D | 0 | 0 |
| Example 69 | N/D | N/D | 17 |
| Example 70 | N/D | N/D | 77 |
| Example 71 | N/D | N/D | 66 |
| Example 72 | N/D | N/D | 16 |
| Example 73 | N/D | N/D | 85 |
| Example 74 | N/D | N/D | 14 |
| Example 75 | N/D | N/D | 58 |
| Example 76 | N/D | N/D | 30 |

* N/D indicates No Data.

As shown in Table 2, it was confirmed that the compounds of Examples 1~76 of the present invention could inhibit the TMPRSS4 serine protease activity dose-dependently by the examination using peptide substrate. The TMPRSS4 serine protease activity was 47~100% inhibited by those compounds of Examples 1~4, 6~11, 13~24, 26~29, 32~34, 36, 37, 52~55, 61~63, 65, at the concentration of 30 µM. Particularly, the compounds of Examples 1, 2, 4, 6, 8, 9, 16, 21~23, 26, 32, 33, 36, 39, 65, 66, 70, 71, 73, 75 could inhibit the activity 51~100% at the concentration of 10 µM.

Therefore, the compounds of the present invention had excellent inhibitory effect on TMPRSS4 serine protease activity, suggesting that they could be effectively used as a composition for preventing or treating cancer by inhibiting TMPRSS4 over-expressed in cancer cells, particularly in lung cancer, colorectal cancer, and stomach cancer cells.

Experimental Example 2

Inhibitory Effect on Infiltration of Cancer Cells Over-Expressing TMPRSS4

The following experiment was performed to investigate the inhibitory effect of the compounds confirmed to have excellent effect of inhibiting TMPRSS4 serine protease activity in Experimental Example 1 on infiltration of cancer cells over-expressing TMPRSS4.

Step 1: Construction of Cancer Cell Line Over-Expressing TMPRSS4

Colorectal cancer cell line SW480 was mixed with 4 µg of pCMV-myc-TMPRSS4 expression vector (Korean Patent No. 10-0906145; Heekyung Jung, et al., *Oncogene*, 27(18), 2635-2647 (2008)) and 10 µl of lipofectamine (Invitrogen, USA) in 2.5 ml of Opti-MEM medium, followed by transfection according to the manufacturer's protocol (Invitrogen, USA). The cells were distributed in a 6-well plate at the density of 3×10$^5$ cells/well, followed by transfection. 48 hours later, the medium was replaced with a selection medium (800 µg/ml G418 medium). G418-resistant clone was separated, followed by culture for 2 weeks, during which selection was performed. As a result, TMPRSS4 over-expressing cell line was constructed.

Step 2: Effect on Cancer Cell Infiltration

The cancer cell line constructed in step 1 was distributed in a 24-well trans-well plate (8 µm pore size; Costar, USA) whose porous membrane was coated with 100 µl of matrigel (BD Biosciences, USA) diluted with serum-free medium at the concentration of 250 µg/ml, which stood at room temperature for 1 hour for solidification. Lower chamber of the transwell plate was coated with 100 µl of collagen type I (Sigma) at the concentration of 20 µg/ml. $4 \times 10^4$ cells resuspended in the serum-free medium containing the compounds of Examples 1~68 of the present invention were distributed in the upper chamber. The serum-free medium containing the compounds of the present invention was distributed in the lower chamber. While culturing the cells in a 37, 5% $CO_2$ incubator for 48 hours, cell migration from the upper chamber to lower chamber was allowed. Those cells that did not migrate were eliminated from the surface of the upper chamber. The cells migrated from the upper chamber to the lower chamber were fixed in 3.7% paraformaldehyde dissolved in PBS, followed by staining with 2% crystal violet solution. The excessive crystal violet solution was washed away with distilled water. The migrated cell number was counted from 5 randomly selected areas (×200). The experiment was repeated at least twice under the same condition, and the representative result was presented.

The inhibitory effect of each compound on the infiltration of TMPRSS4 over-expressing colorectal cancer cell line SW480 was calculated by Mathematical Formula 1, which presents the number of infiltrated cells with % by the number of infiltrated cells in the negative control treated with DMSO. The results are shown in Table 3.

Infiltration Inhibition Rate (%)=100−Infiltrated cell number with the treatment of each compound/ Infiltrated cell number with the treatment of DMSO×100   [Mathematical Formula 1]

TABLE 3

| Formula | Inhibition rate of target-expressing colorectal cancer cell activity (%, 0.1~2 uM) |
|---|---|
| Example 1 | 76 (0.8 uM) |
| Example 6 | 49 (0.8 uM) |
| Example 8 | 72 (0.8 uM) |
| Example 19 | 81 (2 uM) |
| Example 22 | 43 (0.1 uM) |
| Example 25 | 51 (25 uM) |
| Example 27 | 54 (2 uM) |
| Example 28 | 52 (2 uM) |
| Example 32 | 68 (0.8 uM) |
| Example 33 | 43 (0.1 uM) |
| Example 36 | 76 (0.8 uM) |
| Example 37 | 44 (5 uM) |
| Example 53 | 34 (0.1 uM), 56 (1 uM) |
| Example 55 | 26 (0.1 uM) |
| Example 65 | 53 (0.1 uM) |

As shown in Table 3, the compounds of Examples 1, 6, 8, 19, 22, 25, 27, 28, 32, 33, 36, 37, 53, 55 and 65 were confirmed to inhibit the infiltration of colorectal cancer cells expressing TMPRSS4 26~81%. The compounds of Examples 1, 8, 19, 25, 27, 28, 32, 36, 53 and 65 inhibited the infiltration 51~81%. In particular, the compound of Example 19 inhibited the infiltration 81%.

Therefore, the compounds of the present invention had excellent effect of inhibiting the infiltration of cancer cells expressing TMPRSS4, suggesting that they could be effectively used as a composition for preventing or treating cancer owing to their excellent effect of inhibiting cancer cell infiltration.

What is claimed is:

1. A method for inhibiting colorectal cancer metastasis comprising: administrating a pharmaceutically effective dose of a 2-hydroxyarylamide derivative or a pharmaceutically acceptable salt thereof, wherein the 2-hydroxyarylamide derivative is selected from the group consisting of:
- (6) 5-chloro-2-hydroxy-N-(3-methoxy-5-(trifluoromethyl)phenyl)benzamide;
- (19) 5-chloro-N-(4-cyano-3-(trifluoromethyl)phenyl)-2-hydroxybenzamide;
- (25) 5-chloro-2-hydroxy-N-quinoline-3-yl-benzamide;
- (27) 5-chloro-N-(2-chloro-4-cyano-phenyl)-2-hydroxybenzamide;
- (28) 5-chloro-2-hydroxy-N-(5-trifluoromethyl-[1,3,4]thiadiazole-2-yl)-benzamide;
- (32) 5-chloro-N-(4-chloro-3-(trifluoromethyl)phenyl)-2-hydroxybenzamide;
- (36) 5-chloro-2-hydroxy-N-(2-nitro-4-trifluoromethylphenyl)-benzamide;
- (37) 5-chloro-N-(5-cyano-pyridine-2-yl)-2-hydroxy-benzamide; and
- (53) 5-chloro-2-hydroxy-N-(4-phenylthiazole-2-yl)-benzamide;

wherein the 2-hydroxyarylamide derivative or a pharmaceutically acceptable salt thereof inhibits the activity of TMPRSS4 (transmembrane protease serine-4).

2. The method of claim 1, wherein the 2-hydroxyarylamide derivative or a pharmaceutically acceptable salt thereof is administered orally or parenterally.

\* \* \* \* \*